(12) United States Patent
Dalko et al.

(10) Patent No.: US 7,732,414 B2
(45) Date of Patent: *Jun. 8, 2010

(54) C-GLYCOSIDE COMPOUNDS FOR STIMULATING THE SYNTHESIS OF GLYCOSAMINOGLYCANS

(75) Inventors: Maria Dalko, Gif-sur-Yvette (FR); Lionel Breton, Versailles (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/373,485

(22) Filed: Mar. 13, 2006

(65) Prior Publication Data

US 2006/0223763 A1    Oct. 5, 2006

Related U.S. Application Data

(60) Division of application No. 10/463,323, filed on Jun. 18, 2003, now Pat. No. 7,049,300, which is a continuation of application No. PCT/FR01/04166, filed on Dec. 21, 2001.

(30) Foreign Application Priority Data

Dec. 22, 2000 (FR) .................................. 00 16997

(51) Int. Cl.
*A61K 31/7008* (2006.01)
*A61K 31/7024* (2006.01)
*A61K 31/70* (2006.01)

(52) U.S. Cl. .............................. 514/23; 514/24; 514/62
(58) Field of Classification Search ................... 514/23, 514/25, 62
See application file for complete search history.

(56) References Cited

U.S. PATENT DOCUMENTS

| | | | |
|---|---|---|---|
| 4,446,312 A | | 5/1984 | Noyori et al. |
| 5,612,044 A | * | 3/1997 | Suares et al. ................. 424/401 |
| 5,658,880 A | | 8/1997 | Dasgupta et al. |
| 5,660,992 A | | 8/1997 | Dasgupta et al. |
| 5,750,508 A | | 5/1998 | Dasgupta et al. |
| 5,789,385 A | * | 8/1998 | Anderson et al. ............. 514/25 |
| 6,197,752 B1 | | 3/2001 | Schmidt et al. |
| 6,413,936 B1 | | 7/2002 | Schmidt et al. |
| 6,495,147 B1 | | 12/2002 | Dumas et al. |
| 6,613,748 B2 | * | 9/2003 | Bittman et al. ................. 514/42 |
| 7,049,300 B2 | * | 5/2006 | Dalko et al. ................... 514/23 |

FOREIGN PATENT DOCUMENTS

| | | |
|---|---|---|
| EP | 0 295 092 | 12/1988 |
| FR | 2770776 A1 | 5/1999 |
| JP | B S36-014360 | 8/1961 |
| JP | A S57-082386 | 5/1982 |
| JP | A S64-13008 | 1/1989 |
| JP | A H02-124896 | 5/1990 |
| JP | A H09-124679 | 5/1997 |
| JP | A H09-169792 | 6/1997 |
| JP | A H10-17433 | 1/1998 |
| JP | T H11-507020 | 6/1999 |
| JP | A H11-335234 | 12/1999 |
| WO | WO 92/018135 | 10/1992 |
| WO | WO 98/009668 | 3/1998 |
| WO | WO 99/24009 | * 5/1999 |

OTHER PUBLICATIONS

Rodrigues, F., et al., "*a convenient, one-step, synthesis of β-C-glycosidic Ketones in aqueous media*", Chem. Commun., 2000, pp. 2049-2050, The Royal Society of Chemistry, Cambridge, England.

Schönenberger, B., et al., "*Enantioselective Synthesis of Pseudomonic Acids. I. Synthesis of Key Intermediates*", Helvetica Chimica Acta., 1982, pp. 2333-2337, vol. 65, Fasc. 7—Nr. 229, Schweizerische Chemische Gesellschaft, Basel, Switzerland.

Hoffmann, M.G., et al., "*Reaktionen von Glycosyl-trichloroacetimidaten mit silylierten C-Nucleophilen*", Liebigs Ann. Chem. 1985, pp. 2403-2419, VCH Verlagsgesellschaft mbH, D-6940 Weinheim, Germany (English abstract only).

BeMiller, J.N., et al., "*N-Substituted (β-D-galactopyranosylmethyl)amines, and C-β-D-galactopyranosylformamides, and related compounds*", Carbohydrate Research, 1990, pp. 111-126, [200], Elsevier Science Publishers B.V., The Netherlands.

Goekjian, P.G., et al., "*Preferred Conformation of C-Glycosides. 6. Conformational Similarity of Glycosides and Corresponding C-Glycosides*," J. Org. Chem., 1991, pp. 6412-6422, [56], American Chemical Society, USA.

Solomons, "*Fundamentals of Organic Chemistry*", Third Edition, 1990, pp. 333, 667, 671, 681, 786, John Wiley & Sons, USA.

Ault, Addison, "*Techniques and Experiments for Organic Chemistry*", Second Edition, 1976, pp. 36-38, 69-70, Holbrook Press, Inc., Boston, MA, USA.

Aucagne et al., "Synthetic Approaches to C-Glucosinolates," Tetrahedron, vol. 56, pp. 2647-2654 (2000).

Cipolla et al., New easy and Stereoselective Access to C-Glycosides of Glucosamine and Mannosamine, Carbohydrate Letters, vol. 2, pp. 131-136 (1996).

Cipolla et al., Stereoselective synthesis of α-C-Glycosides of N-acetylgalactosamine, Tetrahedron: Asymmetry, vol. 11, pp. 295-303 (2000).

(Continued)

*Primary Examiner*—Shaojia Anna Jiang
*Assistant Examiner*—Ganapathy Krishnan
(74) *Attorney, Agent, or Firm*—Finnegan, Henderson, Farabow, Garrett & Dunner, L.L.P.

(57) ABSTRACT

C-glycoside compounds are suited for stimulating the synthesis of glycosaminoglycans containing a D-glucosamine and/or N-acetyl-D-glucosamine residue, advantageously hyaluronic acid, and/or proteoglycans, advantageously proteoglycans containing hyaluronic acid, by fibroblasts and/or keratinocytes.

20 Claims, No Drawings

OTHER PUBLICATIONS

Cipolla et al., "Synthesis of Stable Analogues of Glyceroglycolipids," Tetrahedron, vol. 53, No. 17, pp. 6163-6170 (1997).

Dale et al., "Reversible Inhibitors of β-Glucosidase," Biochemistry, vol. 24, pp. 3530-3539 (1985).

Elfakir et al., Porous graphitized carbon and octadecyl-silica columns in the separation of some alkylglycoside detergents, Journal of Chromatography A, vol. 782, pp. 191-198 (1997).

Fairweather et al., "The Role of Hydrolases in a Synthesis of Some Epoxyalkyl β-C-Cellobiosides," Tetrahedron, vol. 55, pp. 3695-3706 (1999).

Hagedorn et al., "Syntheis of the deculopyranosic acid analog of N-acetylneuraminic acid, its 5-epimer and 6-epimer, and of 5-acetamido-1,3,5-trideoxy-D-glycero-D-galacto-non-2-ulopyranose," Carbohydrate Research, vol. 236, pp. 89-96 (1992).

Harenbrock et al., Liebigs Annalen, vol. 1, pp. 55-62 (1996).

Hutchinson et al., "On the Behavoir of Some Glucosyl Alkylbenzenes and Glucosyl Alkanes," the Journal of Physical Chemistry, vol. 68, No. 10, pp. 2812-2825 (1964).

Jegou et al., "Stereoselective Synthesis of α-C-D-Gluco- and D-Galactopyranosyl glycosides from an Isoprenoid Synthon," Tetrahedron, vol. 54, pp. 14779-14790 (1998).

Lancelin et al., "Synthesis and Conversions of C-(Alkyn-1-yl)-β-D-Glucopyranosides," Tetrahedron Letters, vol. 24, No. 44, pp. 4833-4836 (1983).

Maity et al., "Design and Synthesis of Mannose Analogues as Inhibitors of α-Mannosidase," Tetrahedron, vol. 50, No. 23, pp. 6965-6974 (1994).

Peri et al., "A highly convergent approach to O- and N-linked glycopetide analogues," Glycoconjugate Journal, vol. 16, pp. 399-404 (1999).

SanMartin et al., "Radical-Mediated Synthesis of α-C-Glycosides Based on N-Acyl Galactosamine," Organic Letters, vol. 2., No. 25, pp. 4051-4054 (2000).

Sun et al., "Synthesis and "Anomerization" of C-Glycosyl Compounds Related to Some Heterocyclic Natural Products," Carbohydrate Research, vol. 171, pp. 35-47 (1987).

Svensson et al., "Purification of α-L-fucosidase by C-glycosylic affinity chromatography, and the enzymatic synthesis of α-L-fucosyl disaccharides," Carbohydrate Research, vol. 200, pp. 391-402 (1990).

Zhdanov et al., "Reaction of Unprotected Aldoses With Acetylmethylenetriphenylphosphorane," Zhurnal Obschei Khimii, col. 39, No. 5, pp. 1121-1124 (May 1969), English Equivalent.

Zhdanov, et al., "Synthesis of new C-glycosides," Doklady Akademii Nauk SSSR, vol. 152(1), pp. 102-105 (1963), Abstract.

Gertsev et al., Farmatsiya, (Moscow, Russian Federation), vol. 29, No. 6, pp. 12-14 (1980).

Wang et al., Huaxue Tongbao, vol. 11, pp. 42-43 (2000).

Official Action dated Jul. 3, 2007, in Japanese Patent Application No. 2002-552923.

Office Action dated Jan. 21, 2005 from parent application, U.S. Appl. No. 10/463,323.

Office Action dated Jul. 13, 2005 from parent application, U.S. Appl. No. 10/463,323.

* cited by examiner

C-GLYCOSIDE COMPOUNDS FOR STIMULATING THE SYNTHESIS OF GLYCOSAMINOGLYCANS

CROSS-REFERENCE TO RELATED APPLICATIONS

This application is a divisional of U.S. patent application Ser. No. 10/463,323, filed Jun. 18, 2003 now U.S. Pat. No. 7,049,300 now allowed, which claims priority under 35 U.S.C. §119 of FR-00/16997, filed Dec. 22, 2000, and is a continuation of PCT/FR01/04166, filed Dec. 21, 2001 and designating the United States (published in the French language on Jul. 4, 2002 as WO 02/051828 A3; the title and abstract were also published in English), all of which are hereby expressly incorporated by reference.

BACKGROUND OF THE INVENTION

1. Technical Field of the Invention

The present invention relates to novel C-glycoside derivatives, to a process for synthesizing these and to compositions comprised thereof.

The present invention also relates to the administration, in a physiologically acceptable medium, in a cosmetic composition or for the preparation of a pharmaceutical composition, of at least one C-glycoside derivative, the compound or the composition being suited to stimulate the synthesis of glycosaminoglycans containing a D-glucosamine and/or N-acetyl-D-glucosamine residue, advantageously hyaluronic acid, and/or proteoglycans, advantageously proteoglycans containing hyaluronic acid, by fibroblasts and/or keratinocytes.

This invention also relates to a cosmetic regime or regimen comprising administering to an individual in need of such treatment such a cosmetic composition.

2. Description of Background/Related/Prior Art

Human skin consists of two compartments, namely, a superficial compartment, the epidermis, and a deep compartment, the dermis.

Natural human epidermis is composed mainly of three types of cell: the keratinocytes, which form the vast majority, the melanocytes and the Langerhans cells. Each of these cell types contributes by virtue of its intrinsic functions, towards the essential role played in the body by the skin.

The dermis gives the epidermis a solid support. It is also the epidermis' nourishing factor. It consists mainly of fibroblasts and of an extracellular matrix. Leukocytes, mastocytes and tissue macrophages are also found in the dermis. It also consists of blood vessels and nerve fibers.

The extracellular matrix of the dermis, like that of all the connective tissues of the body, is composed of proteins belonging to several major families: collagens, matrix glycoproteins other than collagens (fibronectin, laminin), elastin and proteoglycans. Glycosaminoglycans in free form (i.e., not attached to a protein) are also found in the extracellular matrix of the dermis, like that of all the connective tissues of the body.

It is now well established that specific interactions exist between these various classes of proteins to give rise to a functional tissue.

Proteoglycans are complex macromolecules consisting of a branched central protein trunk, or protein network, to which are attached numerous polyoside side chains known as glycosaminoglycans.

Hereinbelow in the present patent application, proteoglycans will be denoted by the abbreviation PG and glycosaminoglycans by the abbreviation GAG.

GAGs have long been referred to by the term acidic mucopolysaccharides on account of their high water-retaining capacity, their carbohydrate nature and their acidic nature derived from the numerous negative charges thereon.

Thus, the polarity of GAGs implicitly makes them participate in certain biological functions, for instance the moisturization of tissues, the fixing of cations or the barrier role of ionic filtration.

PGs and GAGs are synthesized by various cells in the dermis and the epidermis: fibroblasts, keratinocytes and melanocytes.

The fibroblasts mainly synthesize collagens, matrix glycoproteins other than collagens (fibronectin, larinin), proteoglycans and elastin. The keratinocytes mainly synthesize sulfated GAGs and hyaluronic acid, while the melanocytes apparently do not produce any hyaluronic acid.

When they are incorporated in a PG, GAGs are linear chains composed of a repetition of a base diholoside always containing a hexosamine (glucosamine or galactosamine) and another saccharide (glucuronic acid, iduronic acid or galactose). The glucosamine is either N-sulfated or N-acetylated. On the other hand, the galactosamine is always N-acetylated. In addition, there may be sulfates O-bonded to the hexosamine, uronic acid and galactose.

The strong anionic nature of GAGs is explained by the presence of carboxylate groups in the hexuronic acids (glucuronic acid and iduronic acid) and of O- and N-bonded sulfate groups.

The main GAGs are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS), which differs from the other glycosaminoglycans by the presence of galactose in the place of uronic acid.

When they are combined with a protein in the form of PG, the GAGs are linked via anchoring structures to the various polypeptide chains, named the "core" protein or carrier protein, and thus form PG molecules.

GAGs may also exist in the extracellular matrix in free form, i.e., not bound to a matrix protein: this is especially the case for hyaluronic acid.

During the synthesis of PGs, the GAGs are polymerized from these anchoring structures.

The synthesis of GAGs requires the coordinated and concerted action of very specific enzymes (transferases, epimerases and sulfotransferases) that are adjacent in the membrane of the endoplasmic reticulum and of the golgi bodies. Next, a host of biochemical reactions (N-deacetylation, N- and O-sulfation, and epimerization) modify the two constituent saccharides of the base unit, heterogeneously along the chain. For example, from one heparan sulfate chain to another, the glucuronic acid/iduronic acid ratio, the nature, number and position of the O-sulfations, and the N-sulfate/O-sulfate ratio may vary, which essentially offers immense structural diversity.

In general, the biological roles of PGs are highly diversified, ranging from a passive mechanical support function (for example serglycines) or an ionic barrier role in molecular filtration (for example perlecane and bamacane of the glomerular basal membrane), to more specific effects in cell adhesion, spreading, proliferation and differentiation or morphogenesis, or to highly specific effects of PG-protein interactions, such as the beta-glycan receptor function or the interaction of decorin with collagen.

One of the roles of dermal connective tissue is to protect the body against external attack by simultaneously forming an informative interface.

To do this, the dermis has high mechanical strength while maintaining, however, great flexibility.

Its strength is ensured by the dense network of collagen fibers, but it is the PGs and the hyaluronic acid which, by ensuring the moisturization, distribution and suppleness of the fibers, make the difference between the skin and, for example, leather.

The PGs constitute 0.5% to 2% of the dry weight of the dermis, collagen alone representing up to 80% of this weight.

The concentration and distribution in human skin of GAGs and PGs vary with age.

Hyaluronic acid or hyaluronan (HA) is the main GAG of the dermis, the latter containing half the HA of the body.

The synthesis of HA is performed especially by the fibroblasts, close to the inner face of the plasma membrane. It is performed continuously. This gigantic polysaccharide (several million daltons) has a very high intrinsic viscosity, ensuring the moisturization and assembly of the various components of the connective tissue by forming supramolecular complexes.

Dermatan sulfate (DS), which was first isolated from the dermis, is also widely abundant in the skin. It constitutes 40% to 50% of the dermal GAGs.

In parallel with the mechanisms contributing to the development of these specialized extracellular matrices, continuous remodeling processes exist, the regulation of which depends on the balance between the synthesis and degradation of the protein components of the matrix.

Several families of matrix proteases are now described, as are the factors involved in their activation-inactivation.

In the course of chronological and/or actinic aging, the dermis and the epidermis undergo several changes and degradations which are reflected, with age, by flaccidness and a loss of suppleness of the skin.

Among the components degraded (especially collagen and elastin), the PGs and GAGs are also adversely affected. Specifically, over the course of aging, the fibroblasts and keratinocytes produce less and less PGs and GAGs and their synthesis is imperfect. This results in considerable disorganization: the deposition of GAGs on the protein skeleton forming the PG is abnormal, the consequence of this is a reduced avidity for water of these PGs thus a reduction in the moisturization and tonicity of tissues.

Restoring a normal production of PGs and GAGs by fibroblasts and keratinocytes contributes partially towards compensating for the loss of moisturization of the skin.

The degradation of these matrices thus contributes towards the phenomenon of dryness and of loss of suppleness of the skin.

The importance of having available active agents whose effects are directed towards maintaining the level of PGs and GAGs in the skin and thus of maintaining, inter alia, good moisturization and good suppleness of the skin will thus be appreciated.

SUMMARY OF THE INVENTION

It has now surprisingly and unexpectedly been determined that C-glycoside derivatives are capable of increasing the synthesis of glycosaminoglycans containing a D-glucosamine and/or N-acetyl-D-glucosamine residue, advantageously hyaluronic acid, and/or proteoglycans, advantageously proteoglycans containing hyaluronic acid, by fibroblasts and/or keratinocytes.

In the prior art, WO 99/24009 to LVMH describes the use of D-xylose, of esters thereof and of oligosaccharides containing D-xylose to improve the functionality of epidermal cells and more particularly as a cosmetic or dermatological agent for stimulating the synthesis and/or secretion of PGs and/or GAGs by the keratinocytes, especially the epidermal keratinocytes, said agent being incorporated into a cosmetic or pharmaceutical composition.

In addition, U.S. Pat. Nos. 4,446,312 and 4,454,123 describe derivatives of C-β-D-xylopyranoside type of the following formula:

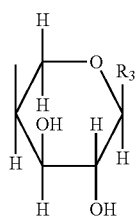

in which $R_3$ represents an alkyl group containing, respectively, from 1 to 5 and from 6 to 25 carbon atoms.

U.S. Pat. Nos. 4,446,312 and 4,454,123 describe that the above-mentioned C-β-D-xylopyranoside compounds induce the biosynthesis of chondroitin sulfate while at the same time reducing the amount of proteoglycan present at the surface of the constituent cell membranes of tissues.

However, to the present inventors' knowledge, the administration of C-glycoside derivatives to stimulate the synthesis of glycosaminoglycans containing a D-glucosamine and/or N-acetyl-D-glucosamine residue, advantageously hyaluronic acid, and/or proteoglycans, advantageously proteoglycans containing hyaluronic acid, by fibroblasts and/or keratinocytes has never been described in the prior art.

The present invention thus features the administration of at least one C-glycoside derivative corresponding to formula (I) below:

in which,
S represents a monosaccharide or a polysaccharide containing up to 20 sugar units, in pyranose and/or furanose form and of L and/or D configuration, the said monosaccharide or polysaccharide containing at least one hydroxyl function that is necessarily free and/or optionally one or more optionally protected amine functions;
the bond S—CH$_2$X represents a bond of anomeric-C nature;
X represents a group chosen from: —CO—, —CH(NR$_1$R$_2$)—, —CHR'—, —C(=CHR')—;
R represents a linear or branched, saturated or unsaturated alkyl, perfluoroalkyl or hydrofluoroalkyl chain, a cycloalkyl, cycloperfluoroalkyl or cyclohydrofluoroalkyl ring containing from 1 to 18 carbon atoms, a phenyl or benzyl radical, the said chain, the said ring or the said radical optionally being interrupted with one or more hetero atoms chosen from oxygen, sulfur, nitrogen and silicon, and optionally substituted with at least one radical chosen from —OR'$_1$, —SR'$_1$, —NR'''$_1$R'$_2$, —COOR''$_2$, —CONHR'''$_2$, —CN, halogen, perfluoroalkyl and hydrofluoroalkyl and/or at least one optionally substituted cycloalkyl, aryl or heterocyclic radical;

R', R$_1$ and R$_2$, which may be identical or different, have the same definition as that given for R, and may also represent a hydrogen and a hydroxyl radical;

R'$_1$, R'$_2$, R''$_1$, R''$_2$, R'''$_1$ and R'''$_2$, which may be identical or different, represent a hydrogen atom or a radical chosen from a linear or branched, saturated or unsaturated alkyl, hydroxyl, perfluoroalkyl and/or hydrofluoroalkyl radical containing from 1 to 30 carbon atoms, formulated into a cosmetic composition comprising a physiologically acceptable medium, the said composition being suited to stimulate the synthesis of glycosaminoglycans containing a D-glucosamine and/or N-acetyl-D-glucosamine residue, advantageously hyaluronic acid, and/or proteoglycans, advantageously proteoglycans containing hyaluronic acid, by fibroblasts and/or keratinocytes.

The present invention also features the administration of at least one C-glycoside derivative of formula (I) as defined above in a cosmetic composition comprising a physiologically acceptable medium, as an agent for stimulating the synthesis of glycosaminoglycans containing a D-glucosamine and/or N-acetyl-D-glucosamine residue, advantageously hyaluronic acid, and/or of proteoglycans, advantageously proteoglycans containing hyaluronic acid, by fibroblasts and/or keratinocytes.

This invention also features the use of a C-glycoside derivative of formula (I) as defined above, for the manufacture of a pharmaceutical or dermatological composition comprising a physiologically acceptable medium, the said composition being suited to stimulate the synthesis of glycosaminoglycans containing a D-glucosamine and/or N-acetyl-D-glucosamine residue, advantageously hyaluronic acid, and/or of proteoglycans, advantageously proteoglycans containing hyaluronic acid, by fibroblasts and/or keratinocytes.

This invention also features the optical and/or geometrical isomers of the C-glycoside derivatives corresponding to formula (I), alone or as a mixture in, all proportions, and also to the physiologically acceptable salts of these derivatives.

DETAILED DESCRIPTION OF BEST MODE AND SPECIFIC/PREFERRED EMBODIMENTS OF THE INVENTION

More particularly according to the present invention, the expression "physiologically acceptable medium" means a medium that is compatible with the skin, mucous membranes, the nails, the scalp and/or the hair.

The anomeric-C bond may be α or β.

According to the invention, the C-glycoside derivatives corresponding to formula (I) may be used alone or as a mixture in any proportion.

According to the invention, the C-glycoside derivatives corresponding to formula (I) may be of natural or synthetic origin, totally or partially purified or any preparation containing them.

The term "natural origin" means a derivative extracted from natural material in which it is present, for example plants. The term "synthetic origin" means a derivative or compound prepared by chemical synthesis or by biotechnology.

The expression "totally or partially purified" means herein that, during its synthesis or with respect to its natural state (fresh or dried plant or cells), the C-glycoside derivative corresponding to formula (I) in the composition of the invention has been concentrated and/or freed, respectively, of at least some of the side reaction products derived from its synthesis or of at least some of the other constituents of the natural material in which it is present.

According to one preferred embodiment of the invention, the C-glycoside derivatives corresponding to formula (I) that are used are those for which R', R$_1$ and R$_2$, which may be identical or different, have the same definition as that given for R, and may also represent a hydroxyl radical.

According to another preferred embodiment of the invention, the C-glycoside derivatives corresponding to formula (I) that are used are those for which S represents a monosaccharide or a polysaccharide containing up to 6 sugar units, in pyranose and/or furanose form and of L and/or D series, the said monosaccharide or polysaccharide containing at least one hydroxyl function that is necessarily free and/or optionally one or more amine functions that are necessarily protected, X and R otherwise retaining all the definitions given above.

Advantageously, the monosaccharides that are preferred are chosen from D-glucose, D-galactose, D-mannose, D-xylose, D-lyxose, L-fucose, L-arabinose, L-rhamnose, D-glucuronic acid, D-galacturonic acid, D-iduronic acid, N-acetyl-D-glucosarmine and N-acetyl-D-galactosainine, and advantageously denotes D-glucose, D-xylose, N-acetyl-D-glucosamine or L-fucose, and very preferentially D-xylose.

Advantageously also, the preferred polysaccharides containing up to 6 sugar units are chosen from D-maltose, D-lactose, D-cellobiose, D-maltotriose, a disaccharide combining a uronic acid chosen from D-iduronic acid and D-glucuronic acid with a hexosamine chosen from D-galactosamine, D-glucosamine, N-acetyl-D-galactosamine and N-acetyl-D-glucosamine, an oligosaccharide containing at least one xylose advantageously chosen from xylobiose, methyl-β-xylobioside, xylotriose, xylotetraose, xylopentaose and xylohexaose and preferably xylobiose, which is composed of two xylose molecules linked via a 1-4 bond.

According to another preferred embodiment of the invention, the C-glycoside derivatives corresponding to formula (I) that are used are those for which X represents a group chosen from —CO—, —CH(OH)—, —CH(NR$_1$R$_2$)—, —CH$_2$— and —C(=CHR')— and very advantageously represents a —CO—, —CH(OH)— or —CH(NH$_2$)— group, S and R otherwise retaining all the definitions given above.

According to yet another preferred embodiment of the invention, the C-glycoside derivatives corresponding to formula (I) that are used are those for which R represents a linear or branched, saturated or unsaturated alkyl, perfluoroalkyl or hydrofluoroalkyl chain, a cycloalkyl, cycloperfluoroalkyl or cyclohydrofluoroalkyl ring containing from 1 to 6 carbon atoms or a phenyl or benzyl radical, the said chain, the said ring or the said radical possibly being optionally interrupted with one or more hetero atoms chosen from oxygen, sulfur, nitrogen and silicon and optionally substituted with at least one radical chosen from —OR'$_1$, —SR''$_1$, —NR'''$_1$R'$_2$, —COOR''$_2$, —CONHR'''$_2$, —CN, halogen, perfluoroalkyl and hydrofluoroalkyl and/or at least one optionally substituted cycloalkyl, aryl or heterocyclic radical, S and X otherwise retaining all the definitions given above.

In another preferred embodiment of the invention, the C-glycoside derivatives corresponding to formula (I) that are used are those for which R', R$_1$ and R$_2$, which may be identical or different, have the same definition as that given for R, and may also represent a hyrogen atom and a hydroxyl radical, S, X and R otherwise retaining all the definitions given above.

In these preferred embodiments of the invention, the C-glycoside derivatives corresponding to formula (I) that are used are those for which R', $R_1$, $R_2$, $R'_1$, $R'_2$, $R''_1$, $R''_2$, $R'''_1$ and $R'''_2$ are defined as above, S, X and R otherwise retaining all the definitions given above.

The expression "all the definitions given above" for S, X and R means herein both the general definitions and the preferred definitions.

Among the C-glycoside derivatives of formula (I) used according to the invention, the ones that are most particularly preferred are:

C-β-D-xylopyranoside-n-propan-2-one;
C-α-D-xylopyranoside-n-propan-2-one;
1-phenyl-2-(C-β-D-xylopyranoside)ethan-1-one;
1-phenyl-2-(C-α-D-xylopyranoside)ethan-1-one;
1-[2-(3-hydroxypropylamino)propyl]-C-β-D-xylopyranose;
1-[2-(3-hydroxypropylamino)propyl]-C-α-D-xylopyranose;
C-β-D-xylopyranoside-2-hydroxypropane;
C-α-D-xylopyranoside-2-hydroxypropane;
C-β-D-xylopyranoside-2-aminopropane;
C-α-D-xylopyranoside-2-aminopropane;
C-β-D-xylopyranoside-2-phenylaminopropane;
C-α-D-xylopyranoside-2-phenylaminopropane;
ethyl 3-methyl-4-(C-β-D-xylopyranoside)butyrate;
ethyl 3-methyl-4-(C-α-D-xylopyranoside)butyrate;
6-(C-β-D-xylopyranoside)-5-ketohexanoic acid;
6-(C-α-D-xylopyranoside)-5-ketohexanoic acid;
6-(C-β-D-xylopyranoside)-5-hydroxyhexanoic acid;
6-(C-α-D-xylopyranoside)-5-hydroxyhexanoic acid;
6-(C-β-D-xylopyranoside)-5-aminohexanoic acid;
6-(C-α-D-xylopyranoside)-5-aminohexanoic acid;
6-(C-β-D-xylopyranoside)-5-phenylaminohexanoic acid;
6-(C-α-D-xylopyranoside)-5-phenylaminohexanoic acid;
1-(C-β-D-xylopyranoside)hexane-2,6-diol;
1-(C-α-D-xylopyranoside)hexane-2,6-diol;
5-(C-β-D-xylopyranoside)-4-ketopentanoic acid;
5-(C-α-D-xylopyranoside)-4-ketopentanoic acid;
5-(C-β-D-xylopyranoside)-4-hydroxypentanoic acid;
5-(C-α-D-xylopyranoside)-4-hydroxypentanoic acid;
5-(C-β-D-xylopyranoside)-4-aminopentanoic acid;
5-(C-α-D-xylopyranoside)-4-aminopentanoic acid;
5-(C-β-D-xylopyranoside)-4-phenylaminopentanoic acid;
5-(C-α-D-xylopyranoside)-4-phenylaminopentanoic acid;
1-(C-β-D-xylopyranoside)pentane-2,5-diol;
1-(C-α-D-xylopyranoside)pentane-2,5-diol;
1-(C-β-D-fucopyranoside)propan-2-one;
1-(C-α-D-fucopyranoside)propan-2-one;
1-(C-β-L-fucopyranoside)propan-2-one;
1-(C-α-L-fucopyranoside)propan-2-one;
1-(C-β-D-fucopyranoside)-2-hydroxypropane;
1-(C-α-D-fucopyranoside)-2-hydroxypropane;
1-(C-β-L-fucopyranoside)-2-hydroxypropane;
1-(C-α-L-fucopyranoside)-2-hydroxypropane;
1-(C-β-D-fucopyranoside)-2-aminopropane;
1-(C-α-D-fucopyranoside)-2-aminopropane;
1-(C-β-L-fucopyranoside)-2-aminopropane;
1-(C-α-L-fucopyranoside)-2-aminopropane;
1-(C-β-D-fucopyranoside)-2-phenylaminopropane;
1-(C-α-D-fucopyranoside)-2-phenylaminopropane;
1-(C-β-L-fucopyranoside)-2-phenylaminopropane;
1-(C-α-L-fucopyranoside)-2-phenylaminopropane;
ethyl 3-methyl4-(C-β-D-fucopyranoside)butyrate;
ethyl 3-methyl4-(C-α-D-fucopyranoside)butyrate;
ethyl 3-methyl-4-(C-β-L-fucopyranoside)butyrate;
ethyl 3-methyl-4-(C-α-L-fucopyranoside)butyrate;
6-(C-β-D-fucopyranoside)-5-ketohexanoic acid;
6-(C-α-D-fucopyranoside)-5-ketohexanoic acid;
6-(C-β-L-fucopyranoside)-5-ketohexanoic acid;
6-(C-α-L-fucopyranoside)-5-ketohexanoic acid;
6-(C-β-D-fucopyranoside)-5-hydroxyhexanoic acid;
6-(C-α-D-fucopyranoside)-5-hydroxyhexanoic acid;
6-(C-β-L-fucopyranoside)-5-hydroxyhexanoic acid;
6-(C-α-L-fucopyranoside)-5-hydroxyhexanoic acid;
6-(C-β-D-fucopyranoside)-5-aminohexanoic acid;
6-(C-α-D-fucopyranoside)-5-amninohexanoic acid;
6-(C-β-L-fucopyranoside)-5-aminohexanoic acid;
6-(C-α-L-fucopyranoside)-5-aminohexanoic acid;
1-(C-β-D-fucopyranoside)hexane-2,6-diol;
1-(C-α-D-fucopyranoside)hexane-2,6-diol;
1-(C-β-L-fucopyranoside)hexane-2,6-diol;
1-(C-α-L-fucopyranoside)hexane-2,6-diol;
5-(C-β-D-fucopyranoside)-4-ketopentanoic acid;
5-(C-α-D-fucopyranoside)-4-ketopentanoic acid;
5-(C-β-L-fucopyranoside)hexane-2,6-diol-4-ketopentanoic acid;
5-(C-α-L-fucopyranoside)hexane-2,6-diol-4-ketopentanoic acid;
5-(C-β-D-fucopyranoside)-4-hydroxypentanoic acid;
5-(C-α-D-fucopyranoside)-4-hydroxypentanoic acid;
5-(C-β-L-fucopyranoside)-4-hydroxypentanoic acid;
5-(C-α-L-fucopyranoside)-4-hydroxypentanoic acid;
5-(C-β-D-fucopyranoside)-4-aminopentanoic acid;
5-(C-α-D-fucopyranoside)-4-aminopentanoic acid;
5-(C-β-L-fucopyranoside)-4-aminopentanoic acid;
5-(C-α-L-fucopyranoside)-4-aminopentanoic acid;
1-(C-β-D-fucopyranoside)pentane-2,5-diol;
1-(C-α-D-fucopyranoside)pentane-2,5-diol;
1-(C-β-L-fucopyranoside)pentane-2,5-diol;
1-(C-α-L-fucopyranoside)pentane-2,5-diol;
1-(C-β-D-glucopyranosyl)-2-hydroxypropane;
1-(C-α-D-glucopyranosyl)-2-hydroxypropane;
1-(C-β-D-glucopyranosyl)-2-aminopropane;
1-(C-α-D-glucopyranosyl)-2-aminopropane;
1-(C-β-D-glucopyranosyl)-2-phenylaminopropane;
1-(C-α-D-glucopyranosyl)-2-phenylaminopropane;
ethyl 3-methyl-4-(C-β-D-glucopyranosyl)butyrate;
ethyl 3-methyl-4-(C-α-D-glucopyranosyl)butyrate;
6-(C-β-D-glucopyranosyl)-5-ketohexanoic acid;
6-(C-α-D-glucopyranosyl)-5-ketohexanoic acid;
6-(C-β-D-glucopyranosyl)-5-hydroxyhexanoic acid;
6-(C-α-D-glucopyranosyl)-5-hydroxyhexanoic acid;
6-(C-β-D-glucopyranosyl)-5-aminohexanoic acid;
6-(C-α-D-glucopyranosyl)-5-aminohexanoic acid;
6-(C-β-D-glucopyranosyl)-5-phenylaminohexanoic acid;
6-(C-α-D-glucopyranosyl)-5-phenylaminohexanoic acid;
1-(C-β-D-glucopyranosyl)hexane-2,6-diol;
1-(C-α-D-glucopyranosyl)hexane-2,6-diol;
5-(C-β-D-glucopyranosyl)-4-ketopentanoic acid;
5-(C-α-D-glucopyranosyl)-4-ketopentanoic acid;
5-(C-β-D-glucopyranosyl)-4-hydroxypentanoic acid;
5-(C-α-D-glucopyranosyl)-4-hydroxypentanoic acid;
5-(C-β-D-glucopyranosyl)-4-aminopentanoic acid;
5-(C-α-D-glucopyranosyl)-4-hydroxypentanoic acid;
5-(C-β-D-glucopyranosyl)-4-phenylaminopentanoic acid;
5-(C-α-D-glucopyranosyl)-4-phenylaminopentanoic acid;
1-(C-β-D-glucopyranosyl)pentane-2,6-diol;
1-(C-α-D-glucopyranosyl)pentane-2,6-diol;
1-(C-β-D-galactopyranosyl)-2-hydroxypropane;
1-(C-α-D-galactopyranosyl)-2-hydroxypropane;
1-(C-β-D-galactopyranosyl)-2-aminopropane;

1-(C-α-D-galactopyranosyl)-2-aminopropane;
1-(C-β-D-galactopyranosyl)-2-phenylaminopropane;
1-(C-α-D-galactopyranosyl)-2-phenylaminopropane;
ethyl 3-methyl-4-(C-β-D-galactopyranosyl)butyrate;
ethyl 3-methyl-4-(C-α-D-galactopyranosyl)butyrate;
6-(C-β-D-galactopyranosyl)-5-ketohexanoic acid;
6-(C-α-D-galactopyranosyl)-5-ketohexanoic acid;
6-(C-β-D-galactopyranosyl)-5-hydroxyhexanoic acid;
6-(C-α-D-galactopyranosyl)-5-hydroxyhexanoic acid;
6-(C-β-D-galactopyranosyl)-5-aminohexanoic acid;
6-(C-α-D-galactopyranosyl)-5-aminohexanoic acid;
6-(C-β-D-galactopyranosyl)-5-phenylaminohexanoic acid;
6-(C-α-D-galactopyranosyl)-5-phenylaminohexanoic acid;
1-(C-β-D-galactopyranosyl)hexane-2,6-diol;
1-(C-α-D-galactopyranosyl)hexane-2,6-diol;
6-(C-β-D-galactopyranosyl)-5-ketopentanoic acid;
6-(C-α-D-galactopyranosyl)-5-ketopentanoic acid;
5-(C-β-D-galactopyranosyl)-4-hydroxypentanoic acid;
5-(C-α-D-galactopyranosyl)-4-hydroxypentanoic acid;
5-(C-β-D-galactopyranosyl)-4-aminopentanoic acid;
5-(C-α-D-galactopyranosyl)-4-aminopentanoic acid;
5-(C-β-D-galactopyranosyl)-4-phenylaminopentanoic acid;
5-(C-α-D-galactopyranosyl)-4-phenylaminopentanoic acid;
1-(C-β-D-galactopyranosyl)pentane-2,6-diol;
1-(C-α-D-galactopyranosyl)pentane-2,6-diol;
1-(C-β-D-fucofuranosyl)propan-2-one;
1-(C-α-D-fucofuranosyl)propan-2-one;
1-(C-β-L-fucofuranosyl)propan-2-one;
1-(C-α-L-fucofuranosyl)propan-2-one;
3'-(acetamido-C-β-D-glucopyranosyl)propan-2'-one;
3'-(acetamido-C-α-D-glucopyranosyl)propan-2'-one;
1-(C-β-D-galactopyranosyl)-2-hydroxypropane;
1-(C-α-D-galactopyranosyl)-2-aminopropane;
1-(acetamido-C-β-D-glucopyranosyl)-2-phenylaminopropane;
1-(acetamido-C-α-D-glucopyranosyl)-2-phenylaminopropane;
ethyl 3-methyl-4-(acetamido-C-β-D-glucopyranosyl)-butyrate;
ethyl 3-methyl-4-(acetamido-C-α-D-glucopyranosyl)-butyrate;
6-(acetamido-C-β-D-glucopyranosyl)-5-ketohexanoic acid;
6-(acetamido-C-α-D-glucopyranosyl)-5-ketohexanoic acid;
6-(acetamido-C-β-D-glucopyranosyl)-5-hydroxyhexanoic acid;
6-(acetamido-C-α-D-glucopyranosyl)-5-hydroxyhexanoic acid;
6-(acetamido-C-β-D-glucopyranosyl)-5-aminohexanoic acid;
6-(acetamido-C-α-D-glucopyranosyl)-5-aminohexanoic acid;
6-(acetamido-C-β-D-glucopyranosyl)-5-phenylaminohexanoic acid;
6-(acetamido-C-α-D-glucopyranosyl)-5-phenylaminohexanoic acid;
1-(acetamido-C-β-D-glucopyranosyl)hexane-2,6-diol;
1-(acetamido-C-α-D-glucopyranosyl)hexane-2,6-diol;
5-(acetamido-C-β-D-glucopyranosyl)-4-ketopentanoic acid;
5-(acetamido-C-α-D-glucopyranosyl)-4-ketopentanoic acid;
5-(acetamido-C-β-D-glucopyranosyl)-4-hydroxypentanoic acid;
5-(acetamido-C-α-D-glucopyranosyl)-4-hydroxypentanoic acid;
5-(acetamido-C-β-D-glucopyranosyl)-4-aminopentanoic acid;
5-(acetamido-C-α-D-glucopyranosyl)-4-aminopentanoic acid;
5-(acetamido-C-β-D-glucopyranosyl)-4-phenylaminopentanoic acid;
5-(acetamido-C-α-D-glucopyranosyl)-4-phenylaminopentanoic acid;
1-(acetamido-C-β-D-glucopyranosyl)pentane-2,6-diol;
1-(acetamido-C-α-D-glucopyranosyl)pentane-2,6-diol.

Thus, the C-glycoside derivatives corresponding to formula (I) have noteworthy activities for stimulating the synthesis of GAGs containing a D-glucosamine and/or N-acetyl-D-glucosamine residue, advantageously hyaluronic acid, and/or PGs, advantageously PGs containing hyaluronic acid, by fibroblasts and/or keratinocytes.

More specifically, it is found that the C-glycoside derivatives of formula (I), on account of their effect of stimulating the synthesis of GAGs containing a D-glucosamine and/or N-acetyl-D-glucosamine residue, advantageously hyaluronic acid, and/or PGs, advantageously PGs containing hyaluronic acid, by fibroblasts and/or keratinocytes, make it possible:

to combat aging of the epidermis. Specifically, it is known that aging of the epidermis is predominantly linked to a loss of hyaluronic acid, to maintain and/or stimulate the moisturization and/or to combat the drying-out of the skin associated with an insufficiency of the action of GAGs, in particular of hyaluronic acid. Such drying-out is observed in particular on aged skin and is essentially associated with a loss of hyaluronic acid, to improve the tonicity of the skin. Specifically, it has been observed that increasing the synthesis of PGs and GAGs makes it possible to create a hydrated cellular environment that is favorable towards exchanges of nutrients, of ions, of cytokine and of growth factors secreted by epidermal cells. Such an environment is also favorable towards eliminating toxic metabolites. This effect is thus reflected by healthy tonic skin, to maintain or restore the suppleness and elasticity of the skin. This effect is associated with stimulating the synthesis of PGs and GAGs, which makes it possible to create a hydrated environment for the matrix constituents, in particular at the dermo-epidermal junction, to promote micro-displacements between the components of this matrix during mechanical stress. Such an effect thus contributes towards making the skin more supple and more elastic, to improve the mineralization of the epidermis, thus making the skin healthier and improving its vitality. This effect is associated with improving the synthesis of GAGs, which ensures good mineralization of the epidermis. Specifically, GAGs can bind ions, via their charged groups, and contribute towards the osmolarity of the epidermis. In this case also, good mineralization of the skin is synonymous with healthy skin showing good vitality, to facilitate intercellular exchanges. This effect is also related to stimulating the synthesis of GAGs, which ensures correct differentiation of the epidermis since a destruction of hyaluronic acid gives rise to an opening of the intercellular spaces and epidermal acanthosis. This effect makes it possible to obtain skin that is more tonic, denser and more compact, to improve the three-dimensional structure of the dermo-epidermal junction. This is also related to improving the synthesis of PGs and GAGs, which ensures the spatial organization of the matrix constituents by reinforcing, for example at the dermo-epidermal junction, the binding between laminin-6 and nidogen (nidogen is a glycoprotein which, with laminin, attaches endothelial cells to type IV collagen), to facilitate cicatrization without forming scars, thus making it possible to repair epidermal micro-traumas which appear when the continuity of the skin is broken. Such an effect makes it possible to combat chapping and the cracked appearance of the skin, to facilitate the migration of keratinocytes, allowing the formation of a horny layer of good quality, to modulate the action of the growth factors and cytokines produced by skin cells. Such an effect affords the cells the signals they need to carry out their function.

The present invention thus features administration, in a cosmetic composition comprising a physiologically acceptable medium, of at least one C-glycoside derivative corresponding to formula (I) as defined above, the derivative or the composition being suited to contribute towards at least one of the following activities:

combating aging of the epidermis, maintaining and/or stimulating the moisturization and/or combating the drying-out of the skin associated with an insufficiency in the action of GAGs containing a D-glucosamine and/or N-acetyl-D-glucosamine residue, in particular hyaluronic acid, improving the tonicity of the skin, maintaining or restoring the suppleness and elasticity of the skin, improving the mineralization of the epidermis, thus making the skin healthier and improving its vitality, facilitating intercellular exchanges, combating chapping and the cracked appearance of the skin.

This invention also features the use of at least one C-glycoside derivative corresponding to formula (I) as defined above, for the manufacture of a pharmaceutical composition, especially a dermatological composition, comprising a physiologically acceptable medium, the said composition being suited to treat insufficiencies in the synthesis of GAGs containing a D-glucosamine and/or N-acetyl-D-glucosamine residue, advantageously hyaluronic acid, and/or of PGs, advantageously PGs containing hyaluronic acid, by fibroblasts and/or keratinocytes, in order to correct the negative effects of the said insufficiencies, in particular to improve the functional state of the cells of the skin, especially of the epidermis.

This pharmaceutical composition may be suited in particular to facilitate cicatrization and to repair epidermal micro-traumas or to treat cutaneous ulceration, in particular ulceration of the legs, or to reduce pregnancy stretch marks.

The amount of C-glycoside derivatives of formula (I) that may be administered according to the invention obviously depends on the desired effect and may thus vary within a wide range.

To provide an order of magnitude, at least one C-glycoside derivative of formula (I) may be used according to the invention in an amount representing from 0.00001% to 25% of the total weight of the composition and preferably in an amount representing from 0.0001% to 10% of the total weight of the composition.

To maintain and/or stimulate the moisturization and/or suppleness and elasticity of the skin and/or mucous membranes, to combat aging of the epidermis, to maintain and/or stimulate moisturization and/or to combat drying-out, to improve the tonicity of the skin, to maintain or restore the suppleness and elasticity of the skin, to improve the mineralization of the epidermis, thus making the skin healthier and improving its vitality, to facilitate intercellular exchanges, to improve the three-dimensional structure of the dermo-epidermal junction, to improve cicatrization without forming scars, to facilitate the migration of keratinocytes, allowing the formation of a horny layer of good quality, to modulate the action of the growth factors and/or cytokines produced by the skin cells, by stimulating the synthesis of GAGS containing a D-glucosamine and/or N-acetyl-D-glucosamine residue, advantageously hyaluronic acid, and/or PGs, advantageously PGs containing hyaluronic acid, the cosmetic composition according to the invention is to be topically applied to the skin of an individual and is optionally left in contact for several hours and is optionally rinsed off.

Thus, the present invention also features a cosmetic regime or regimen for treating the skin and/or the scalp and/or mucous membranes, which is suited to:

combat aging of the epidermis, maintain and/or stimulate the moisturization and/or combat the drying-out of the skin associated with an insufficiency of the action of GAGs containing a D-glucosamine and/or N-acetyl-D-glucosamine residue, in particular hyaluronic acid, improve the tonicity of the skin, maintain or restore the suppleness and elasticity of the skin, improve the mineralization of the epidermis, thus making the skin healthier and improving its vitality, facilitate intercellular exchanges, combat chapping and the cracked appearance of the skin, wherein a cosmetic composition comprising at least one C-glycoside derivative corresponding to formula (I) is topically applied to the skin and/or the scalp and/or mucous membranes, is maintained in contact with the skin and/or mucous membranes and/or the scalp, and is optionally rinsed off.

The treatment process has the characteristics of a cosmetic process insofar as it makes it possible to improve the appearance or comfortable nature of the skin and/or mucous membranes and/or scalp.

There have been huge developments in the chemistry of C-glycoside derivatives in the last twenty years.

Two main reasons account for this interest, namely:

in contrast with O-glycoside derivatives, C-glycoside derivatives are entirely stable in biological media since they are non-metabolizable;

it has moreover been shown that C-glycoside structures have conformational properties very similar to those of their O-glycoside analogs (see in particular the publication "*C-Glycoside Synthesis*" Postema M. H. D., CRC Press. 1995).

C-Glycoside derivatives are well known in the scientific literature; mention may be made especially of the following publications:

Allevi et al. (*J. Chem. Soc., Chem. Commun.*, 1987, pp. 101-102) which describes C-glucopyranosyl derivatives;

Nakamura et al. (*Tetrahedron Letters*, 1996, 37, pp. 3153-3156);

Tsang et al. (*J. Org. Chem.* 1985, 50, pp. 4659- 4661) describes bicyclic pyranose derivatives;

Lay et al. (*J. Chem. Soc., Perkin Trans. I.*, 1994, pp. 333-338) which describes disaccharide derivatives;

Karagiri et al. (*J. Chem. Soc., Perkin Trans. I.*, 1984, pp. 553-560) which describes pyranosofurines and derivatives thereof; and Clingerman et al. (*J. Org. Chem.* 1983, 48, pp. 3141-3146) which describes ribofuranosyl derivatives.

Most of the C-glycoside derivatives described in the prior art have hydroxyl functions that are always protected. These known products are prepared by synthetic methods which are particularly laborious since, in all cases, they involve protecting the hydroxyl functions.

To the knowledge of the present inventors, very few documents describe C-glycoside derivatives containing unprotected hydroxyl functions.

Mention may be made of the following publications.

Document J. Chem. Soc., Perkin Trans. I, 1994, pages 2647-2655 describes a synthetic process leading especially to the following two C-glycoside derivatives:
- 1-(2-acetamido-2-deoxy-α-D-galactopyranosyl) octane, and
- 1-(2-acetamido-2-deoxy-α-D-glucopyranosyl)octane.

The document Liebigs Ann. Chem. 1985, pages 2403-2419 describes a synthetic process in which 1-(α-D-glucopyranosyl)-2-phenylethane is transiently formed.

Document J. Org. Chem. 1991, 56, pages 6412- 6422 describes a synthetic process leading especially to the following C-glycoside derivatives:
- 1-(α-C-D-glucopyranosyl)propane;
- 1-(β-C-D-glucopyranosyl)propane;
- 1-(α-C-D-glucopyranosyl)-2,3-propanediol;
- 1-(β-C-D-glucopyranosyl)-2,3-propanediol;
- 1-(2-deoxy-α-C-D-glucopyranosyl)-2,3-propanediol;
- 1-(2-deoxy-β-C-D-glucopyranosyl)-2,3-propanediol.

Document J. Org. Chem. 1991, 56, pages 6422-6434 describes NMR conformational studies and a synthetic process leading especially to the following two 1,6-bonded C-disaccharide derivatives:

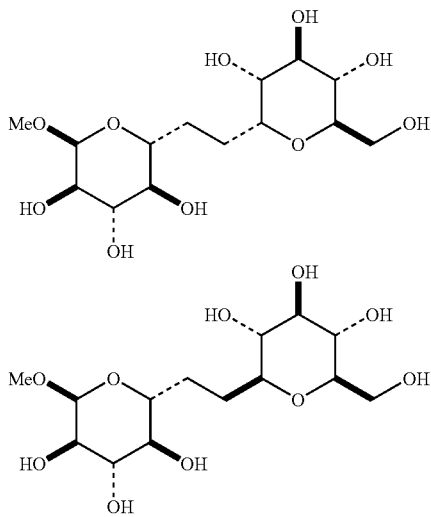

Document Carbohydrate Research, 200 (1990) pages 11-126 describes a synthetic process leading especially to 1-(C-β-D-galactopyranosyl)propane.

Document Helvetica Chimica Acta, vol. 65, Fasc. 7 (1982), No. 229, pages 2333-2237 describes a synthetic process leading especially to 1-(C-β-D-ribopyranosyl)-n-propanone.

As mentioned above, U.S. Pat. Nos. 4,446,312 and 4,454,123 also describe derivatives of C-β-D-xylopyranoside type.

The C-glycoside derivatives described in a document published by Rodrigues, F. et al., "*A convenient, one-step, synthesis of 62-C-glycosidic ketones in aqueous media,*" Chem. Commun., pp. 2049-2050 (2000) are:
- 3'-(β-D-glucopyranosyl)propan-2'-one,
- 3'-(β-D-mannopyranosyl)propan-2'-one, and
- 3'-(D-glucopyranosyl-(1-4)-β-D-glucopyranosyl) propan-2'-one.

These three C-glycoside derivatives are obtained quantitatively in alkaline aqueous medium by condensation of pentane-2,4-dione with D-glucose, D-mannose or D-cellobiose, respectively.

The present inventors have now synthesized novel C-glycoside derivatives corresponding to formula (II) which are capable of stimulating the synthesis of GAGs containing a D-glucosamine and/or N-acetyl-D-glucosamine residue, advantageously hyaluronic acid, and/or PGs, advantageously PGs containing hyaluronic acid, by fibroblasts and/or keratinocytes, and which are readily available in synthetic terms by especially performing a process described in the above-mentioned document published on the Internet or a process modified from this reference.

Thus, the present invention also features novel C-glycoside derivatives corresponding to formula (II) below:

S, X and R having the same definitions as those given above for the C-glycoside derivatives of formula (I), it being understood that S is other than D-glucose, D-cellobiose and D-mannose when X represents a —CO— group and R represents a methyl, and with the exception of the derivatives of formula (II) chosen from:
- 1-(2-acetamido-2-deoxy-α-D-galactopyranosyl) octane;
- 1-(2-acetamido-2-deoxy-α-D-glucopyranosyl)octane;
- 1-(α-D-glucopyranosyl)-2-phenylethane;
- 1-(α-C-D-glucopyranosyl)propane;
- 1-(β-C-D-glucopyranosyl)propane;
- 1-(α-C-D-glucopyranosyl)-2,3-propanediol;
- 1-(β-C-D-glucopyranosyl)-2,3-propanediol;
- 1-(2-deoxy-α-C-D-glucopyranosyl)-2,3-propanediol;
- 1-(2-deoxy-β-C-D-glucopyranosyl)-2,3-propanediol;
- 1-(C-β-D-galactopyranosyl)propane;
- 1-(C-β-D-ribopyranosyl)-n-propanone;
- C-β-D-xylopyranoside derivatives of the following formula:

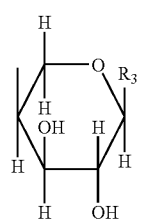

in which $R_3$ represents an alkyl group containing from 3 to 20 carbon atoms;

the following two 1,6-bonded C-disaccharide derivatives:

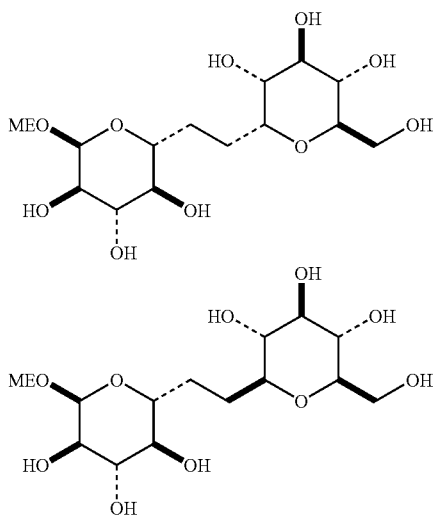

This invention also features the optical and geometrical isomers, alone or as a mixture, in all proportions, and to the physiologically acceptable salts of these derivatives.

According to one preferred embodiment of the invention, the C-glycoside derivatives corresponding to formula (II) that are preferred are those for which S represents a monosaccharide or a polysaccharide containing up to 6 sugar units, in pyranose and/or furanose form and of L and/or D series, the said monosaccharide or polysaccharide containing at least one hydroxyl function that is necessarily free and/or optionally one or more amine functions that are necessarily protected, X and R otherwise retaining all the definitions given above.

Advantageously, the preferred monosaccharides are chosen from D-glucose, D-galactose, D-mannose, D-xylose, D-lyxose, L-fucose, L-arabinose, L-rhamnose, D-glucuronic acid, D-galacturonic acid, D-iduronic acid, N-acetyl-D-glucosamine and N-acetyl-D-galactosamine, and advantageously denotes D-glucose, D-xylose, N-acetyl-D-glucosamine or L-fucose, and very preferentially D-xylose.

Advantageously also, the preferred polysaccharides containing up to 6 sugar units are chosen from D-maltose, D-lactose, D-cellobiose, D-maltotriose, a disaccharide combining a uronic acid chosen from D-iduronic acid and D-glucuronic acid with a hexosamine chosen from D-galactosamine, D-glucosamine, N-acetyl-D-galactosamine and N-acetyl-D-glucosamine, an oligosaccharide containing at least one xylose advantageously chosen from xylobiose, methyl-β-xylobioside, xylotriose, xylotetraose, xylopentaose and xylohexaose, and preferentially xylobiose, which is composed of two xylose molecules linked via a 1-4 bond.

According to another preferred embodiment of the invention, the C-glycoside derivatives corresponding to formula (II) that are used are those for which X represents a group chosen from —CO—, —CH(OH)—, —CH($NR_1R_2$)—, —$CH_2$— and —C(=CHR')— and very advantageously represents a —CO—, —CH(OH)— or —CH($NH_2$)— group, S and R otherwise retaining all the definitions given above.

According to yet another preferred embodiment of the invention, the C-glycoside derivatives corresponding to formula (II) that are used are those for which R represents a linear or branched, saturated or unsaturated alkyl, perfluoroalkyl or hydrofluoroalkyl chain, a cycloalkyl, cycloperfluoroalkyl or cyclohydrofluoroalkyl ring containing from 1 to 6 carbon atoms, the said chain possibly being optionally interrupted with one or more hetero atoms chosen from oxygen, sulfur, nitrogen and silicon, and optionally substituted with at least one radical chosen from —OR'$_1$, —SR"$_1$, —NR'''$_1$R'$_2$, —COOR"$_2$, —CONHR'''$_2$, —CN, halogen, perfluoroalkyl and hydrofluoroalkyl and/or at least one optionally substituted cycloalkyl, aryl or heterocyclic radical, S and X otherwise retaining all the definitions given above; the said ring possibly being optionally interrupted with one or more hetero atoms chosen from oxygen, sulfur, nitrogen and silicon, and optionally substituted with at least one radical chosen from —SR"$_1$, —NR'''$_1$R'$_2$, —COOR"$_2$, —CONHR'''$_2$, —CN, halogen, perfluoroalkyl and hydrofluoroallyl and/or at least one optionally substituted cycloalkyl, aryl or heterocyclic radical, S and X otherwise retaining all the definitions given above; the said ring also possibly being interrupted with one or more hetero atoms chosen from sulfur, nitrogen and silicon, and optionally substituted with at least one radical chosen from —OR'$_1$, —SR"$_1$, —NR'''$_1$R'$_2$, —COOR"$_2$, —CONHR'''$_2$, —CN, halogen, perfluoroalkyl and hydrofluoroalkyl and/or at least one optionally substituted cycloalkyl, aryl or heterocyclic radical, S and X otherwise retaining all the definitions given above.

In another preferred embodiment of the invention, the C-glycoside derivatives corresponding to formula (II) that are used are those for which R', $R_1$ and $R_2$, which may be identical or different, have the same definition as that given for R, and may also represent a hydrogen atom and a hydroxyl radical, S, X and R otherwise retaining all the definitions given above.

Advantageously, the C-glycoside derivatives corresponding to formula (II) that are used are those for which R', $R_1$ and $R_2$, which may be identical or different, have the same definition as that given for R, and may also represent a hydroxyl radical, S, X and R otherwise retaining all the definitions given above.

In these preferred embodiments of the invention, the C-glycoside derivatives corresponding to formula (II) that are used are those for which R', $R_1$, $R_2$, R'$_1$, R'$_2$, R"$_1$, R"$_2$, R'''$_1$ and R'''$_2$ are defined as above, S, X and R otherwise retaining all the definitions given above.

Among the C-glycoside derivatives of formula (II) according to the invention, the ones that are most particularly preferred are:

C-β-D-xylopyranoside-n-propan-2-one;
C-α-D-xylopyranoside-n-propan-2-one;
1-phenyl-2-(C-β-D-xylopyranoside)ethan-1-one;
1-phenyl-2-(C-α-D-xylopyranoside)ethan-1-one;
1-[2-(3-hydroxypropylamino)propyl]-C-β-D-xylopyranose;
1-[2-(3-hydroxypropylamino)propyl]-C-α-D-xylopyranose;
C-β-D-xylopyranoside-2-hydroxypropane;
C-α-D-xylopyranoside-2-hydroxypropane;
C-β-D-xylopyranoside-2-aminopropane;
C-α-D-xylopyranoside-2-aminopropane;
C-β-D-xylopyranoside-2-phenylaminopropane;
C-α-D-xylopyranoside-2-phenylaminopropane;
ethyl 3-methyl-4-(C-β-D-xylopyranoside)butyrate;
ethyl 3-methyl-4-(C-α-D-xylopyranoside)butyrate;
6-(C-β-D-xylopyranoside)-5-ketohexanoic acid;
6-(C-α-D-xylopyranoside)-5-ketohexanoic acid;
6-(C-β-D-xylopyranoside)-5-hydroxyhexanoic acid;
6-(C-α-D-xylopyranoside)-5-hydroxyhexanoic acid;
6-(C-β-D-xylopyranoside)-5-aminohexanoic acid;
6-(C-α-D-xylopyranoside)-5-aminohexanoic acid;
6-(C-β-D-xylopyranoside)-5-phenylaminohexanoic acid;

6-(C-α-D-xylopyranoside)-5-phenylaminohexanoic acid;
1-(C-β-D-xylopyranoside)hexane-2,6-diol;
1-(C-α-D-xylopyranoside)hexane-2,6-diol;
5-(C-β-D-xylopyranoside)-4-ketopentanoic acid;
5-(C-α-D-xylopyranoside)-4-ketopentanoic acid;
5-(C-β-D-xylopyranoside)-4-hydroxypentanoic acid;
5-(C-α-D-xylopyranoside)-4-hydroxypentanoic acid;
5-(C-β-D-xylopyranoside)-4-aminopentanoic acid;
5-(C-α-D-xylopyranoside)-4-aminopentanoic acid;
5-(C-β-D-xylopyranoside)-4-phenylaminopentanoic acid;
5-(C-α-D-xylopyranoside)-4-phenylaminopentanoic acid;
1-(C-β-D-xylopyranoside)pentane-2,5-diol;
1-(C-α-D-xylopyranoside)pentane-2,5-diol;
1-(C-β-D-fucopyranoside)propan-2-one;
1-(C-α-D-fucopyranoside)propan-2-one;
1-(C-β-L-fucopyranoside)propan-2-one;
1-(C-α-L-fucopyranoside)propan-2-one;
1-(C-β-D-fucopyranoside)-2-hydroxypropane;
1-(C-α-D-fucopyranoside)-2-hydroxypropane;
1-(C-β-L-fucopyranoside)-2-hydroxypropane;
1-(C-α-L-fucopyranoside)-2-hydroxypropane;
1-(C-β-D-fucopyranoside)-2-aminopropane;
1-(C-α-D-fucopyranoside)-2-aminopropane;
1-(C-β-L-fucopyranoside)-2-aminopropane;
1-(C-α-L-fucopyranoside)-2-aminopropane;
1-(C-β-D-fucopyranoside)-2-phenylaminopropane;
1-(C-α-D-fucopyranoside)-2-phenylaminopropane;
1-(C-β-L-fucopyranoside)-2-phenylaminopropane;
1-(C-α-L-fucopyranoside)-2-phenylaminopropane;
ethyl 3-methyl4-(C-β-D-fucopyranoside)butyrate;
ethyl 3-methyl4-(C-α-D-fucopyranoside)butyrate;
ethyl 3-methyl-4-(C-β-L-fucopyranoside)butyrate;
ethyl 3-methyl-4-(C-α-L-fucopyranoside)butyrate;
6-(C-β-D-fucopyranoside)-5-ketohexanoic acid;
6-(C-α-D-fucopyranoside)-5-ketohexanoic acid;
6-(C-β-L-fucopyranoside)-5-ketohexanoic acid;
6-(C-α-L-fucopyranoside)-5-ketohexanoic acid;
6-(C-β-D-fucopyranoside)-5-hydroxyhexanoic acid;
6-(C-α-D-fucopyranoside)-5-hydroxyhexanoic acid;
6-(C-β-L-fucopyranoside)-5-hydroxyhexanoic acid;
6-(C-α-L-fucopyranoside)-5-hydroxyhexanoic acid;
6-(C-β-D-fucopyranoside)-5-aminohexanoic acid;
6-(C-α-D-fucopyranoside)-5-amninohexanoic acid;
6-(C-β-L-fucopyranoside)-5-aminohexanoic acid;
6-(C-α-L-fucopyranoside)-5-aminohexanoic acid;
1-(C-β-D-fucopyranoside)hexane-2,6-diol;
1-(C-α-D-fucopyranoside)hexane-2,6-diol;
1-(C-β-L-fucopyranoside)hexane-2,6-diol;
1-(C-α-L-fucopyranoside)hexane-2,6-diol;
5-(C-β-D-fucopyranoside)-4-ketopentanoic acid;
5-(C-α-D-fucopyranoside)-4-ketopentanoic acid;
5-(C-β-L-fucopyranoside)hexane-2,6-diol-4-ketopentanoic acid;
5-(C-α-L-fucopyranoside)hexane-2,6-diol-4-ketopentanoic acid;
5-(C-β-D-fucopyranoside)-4-hydroxypentanoic acid;
5-(C-α-D-fucopyranoside)-4-hydroxypentanoic acid;
5-(C-β-L-fucopyranoside)-4-hydroxypentanoic acid;
5-(C-α-L-fucopyranoside)-4-hydroxypentanoic acid;
5-(C-β-D-fucopyranoside)-4-aminopentanoic acid;
5-(C-α-D-fucopyranoside)-4-aminopentanoic acid;
5-(C-β-L-fucopyranoside)-4-aminopentanoic acid;
5-(C-α-L-fucopyranoside)-4-aminopentanoic acid;
1-(C-β-D-fucopyranoside)pentane-2,5-diol;
1-(C-α-D-fucopyranoside)pentane-2,5-diol;
1-(C-β-L-fucopyranoside)pentane-2,5-diol;
1-(C-α-L-fucopyranoside)pentane-2,5-diol;
1-(C-β-D-glucopyranosyl)-2-hydroxypropane;
1-(C-α-D-glucopyranosyl)-2-hydroxypropane;
1-(C-β-D-glucopyranosyl)-2-aminopropane;
1-(C-α-D-glucopyranosyl)-2-aminopropane;
1-(C-β-D-glucopyranosyl)-2-phenylaminopropane;
1-(C-α-D-glucopyranosyl)-2-phenylaminopropane;
ethyl 3-methyl-4-(C-β-D-glucopyranosyl)butyrate;
ethyl 3-methyl-4-(C-α-D-glucopyranosyl)butyrate;
6-(C-β-D-glucopyranosyl)-5-ketohexanoic acid;
6-(C-α-D-glucopyranosyl)-5-ketohexanoic acid;
6-(C-β-D-glucopyranosyl)-5-hydroxyhexanoic acid;
6-(C-α-D-glucopyranosyl)-5-hydroxyhexanoic acid;
6-(C-β-D-glucopyranosyl)-5-aminohexanoic acid;
6-(C-α-D-glucopyranosyl)-5-aminohexanoic acid;
6-(C-β-D-glucopyranosyl)-5-phenylaminohexanoic acid;
6-(C-α-D-glucopyranosyl)-5-phenylaminohexanoic acid;
1-(C-β-D-glucopyranosyl)hexane-2,6-diol;
1-(C-α-D-glucopyranosyl)hexane-2,6-diol;
6-(C-β-D-glucopyranosyl)-5-ketopentanoic acid;
6-(C-α-D-glucopyranosyl)-5-ketopentanoic acid;
6-(C-β-D-glucopyranosyl)-5-hydroxypentanoic acid;
6-(C-α-D-glucopyranosyl)-5-hydroxypentanoic acid;
6-(C-β-D-glucopyranosyl)-5-aminopentanoic acid;
6-(C-α-D-glucopyranosyl)-5-hydroxypentanoic acid;
6-(C-β-D-glucopyranosyl)-5-phenylaminopentanoic acid;
6-(C-α-D-glucopyranosyl)-5-phenylaminopentanoic acid;
1-(C-β-D-glucopyranosyl)pentane-2,6-diol;
1-(C-α-D-glucopyranosyl)pentane-2,6-diol;
1-(C-β-D-galactopyranosyl)-2-hydroxypropane;
1-(C-α-D-galactopyranosyl)-2-hydroxypropane;
1-(C-β-D-galactopyranosyl)-2-aminopropane;
1-(C-α-D-galactopyranosyl)-2-aminopropane;
1-(C-β-D-galactopyranosyl)-2-phenylaminopropane;
1-(C-α-D-galactopyranosyl)-2-phenylaminopropane;
ethyl 3-methyl-4-(C-β-D-galactopyranosyl)butyrate;
ethyl 3-methyl-4-(C-α-D-galactopyranosyl)butyrate;
6-(C-β-D-galactopyranosyl)-5-ketohexanoic acid;
6-(C-α-D-galactopyranosyl)-5-ketohexanoic acid;
6-(C-β-D-galactopyranosyl)-5-hydroxyhexanoic acid;
6-(C-α-D-galactopyranosyl)-5-hydroxyhexanoic acid;
6-(C-β-D-galactopyranosyl)-5-aminohexanoic acid;
6-(C-α-D-galactopyranosyl)-5-aminohexanoic acid;
6-(C-β-D-galactopyranosyl)-5-phenylaminohexanoic acid;
6-(C-α-D-galactopyranosyl)-5-phenylaminohexanoic acid;
1-(C-β-D-galactopyranosyl)hexane-2,6-diol;
1-(C-α-D-galactopyranosyl)hexane-2,6-diol;
6-(C-β-D-galactopyranosyl)-5-ketopentanoic acid;
6-(C-α-D-galactopyranosyl)-5-ketopentanoic acid;
6-(C-β-D-galactopyranosyl)-5-hydroxypentanoic acid;
6-(C-α-D-galactopyranosyl)-5-hydroxypentanoic acid;
6-(C-β-D-galactopyranosyl)-5-aminopentanoic acid;
6-(C-α-D-galactopyranosyl)-5-aminopentanoic acid;
6-(C-β-D-galactopyranosyl)-5-phenylaminopentanoic acid;
6-(C-α-D-galactopyranosyl)-5-phenylaminopentanoic acid;
1-(C-β-D-galactopyranosyl)pentane-2,6-diol;
1-(C-α-D-galactopyranosyl)pentane-2,6-diol;
1-(C-β-D-fucofuranosyl)propan-2-one;
1-(C-β-D-fucofuranosyl)propan-2-one;
1-(C-β-L-fucofuranosyl)propan-2-one;
1-(C-α-L-fucofuranosyl)propan-2-one;
3'-(acetamido-C-β-D-glucopyranosyl)propan-2'-one;

1-(C-α-L-fucopyranoside)pentane-2,5-diol;
1-(C-β-D-glucopyranosyl)-2-hydroxypropane;
1-(C-α-D-glucopyranosyl)-2-hydroxypropane;
1-(C-β-D-glucopyranosyl)-2-aminopropane;
1-(C-α-D-glucopyranosyl)-2-aminopropane;
1-(C-β-D-glucopyranosyl)-2-phenylaminopropane;
1-(C-α-D-glucopyranosyl)-2-phenylaminopropane;

3'-(acetamido-C-α-D-glucopyranosyl)propan-2'-one;
1-(C-β-D-galactopyranosyl)-2-hydroxypropane;
1-(C-α-D-galactopyranosyl)-2-aminopropane;
1-(acetamido-C-β-D-glucopyranosyl)-2-phenylaminopropane;
1-(acetamido-C-α-D-glucopyranosyl)-2-phenylaminopropane;
ethyl 3-methyl-4-(acetamido-C-β-D-glucopyranosyl)-butyrate;
ethyl 3-methyl-4-(acetamido-C-α-D-glucopyranosyl)-butyrate;
6-(acetamido-C-β-D-glucopyranosyl)-5-ketohexanoic acid;
6-(acetamido-C-α-D-glucopyranosyl)-5-ketohexanoic acid;
6-(acetamido-C-β-D-glucopyranosyl)-5-hydroxyhexanoic acid;
6-(acetamido-C-α-D-glucopyranosyl)-5-hydroxyhexanoic acid;
6-(acetamido-C-β-D-glucopyranosyl)-5-aminohexanoic acid;
6-(acetamido-C-α-D-glucopyranosyl)-5-aminohexanoic acid;
6-(acetamido-C-β-D-glucopyranosyl)-5-phenylaminohexanoic acid;
6-(acetamido-C-α-D-glucopyranosyl)-5-phenylaminohexanoic acid;
1-(acetamido-C-β-D-glucopyranosyl)hexane-2,6-diol;
1-(acetamido-C-α-D-glucopyranosyl)hexane-2,6-diol;
6-(acetamido-C-β-D-glucopyranosyl)-5-ketopentanoic acid;
6-(acetamido-C-α-D-glucopyranosyl)-5-ketopentanoic acid;
6-(acetamido-C-β-D-glucopyranosyl)-5-hydroxypentanoic acid;
6-(acetamido-C-α-D-glucopyranosyl)-5-hydroxypentanoic acid;
6-(acetamido-C-β-D-glucopyranosyl)-5-aminopentanoic acid;
6-(acetamido-C-α-D-glucopyranosyl)-5-aminopentanoic acid;
6-(acetamido-C-β-D-glucopyranosyl)-5-phenylaminopentanoic acid;
6-(acetamido-C-α-D-glucopyranosyl)-5-phenylaminopentanoic acid;
1-(acetamido-C-β-D-glucopyranosyl)pentane-2,6-diol;
1-(acetamido-C-α-D-glucopyranosyl)pentane-2,6-diol.

Moreover, the C-glycoside derivatives of formula (II) for which X corresponds to —CO— constitute synthetic intermediates that are particularly advantageous, specifically on account of the presence of this reactive —CO— group, which makes it possible to obtain C-glycoside derivatives of formula (II) for which X corresponds to —CH(OH)—, —CH(NR$_1$R$_2$)—, —CHR'— or —C(=CHR')—, as described below.

The C-glycoside derivatives of formula (II) for which X corresponds to —CO— are obtained especially via a synthetic process which is an adaptation of the one described in the above-mentioned document published on the Internet.

The formation of C-glycoside derivatives of formula (II) for which X corresponds to —CO— results from the condensation of a β-diketone onto a monosaccharide or a polysaccharide containing up to sugar units, in pyranose and/or furanose form and of L and/or D series, the said monosaccharide or polysaccharide containing at least one hydroxyl function that is necessarily free and/or optionally one or more amine functions that are necessarily protected.

Thus, the present invention also features a process for preparing novel C-glycoside derivatives corresponding to formula (II) as defined above and for which X corresponds to —CO—, comprising:

dissolving, in water or in a mixture consisting of water and a water-miscible solvent, preferably a polar protic solvent, advantageously tetrahydrofuran, dioxane, N-methylpyrrolidine, dimethylformamide, acetonitrile and/or alcohols, in particular ethanol, 1 equivalent of a monosaccharide or a polysaccharide of formula S as defined above, adding between 1 and 2 equivalents and preferably between 1 and 1.2 equivalents of a β-diketone compound of general formula R"—CO—CH$_2$—CO—R, with R as defined above and R" corresponding to the definition given above for R', with the exception of hydrogen, and between 1 and 2 equivalents and preferably between 1 and 1.2 equivalents of an organic or mineral base, preferably a mineral base, and heating the reaction mixture to a temperature of between 40° and 100° C. and preferably between 75° and 90° C., for a period of between 3 and 30 hours and preferably between 5 and 15 hours, then, after cooling, washing the reaction medium with an organic solvent that may be chosen from ethyl acetate, dichloromethane, diethyl ether, diisopropyl ether, tert-butyl methyl ether, and methyl ethyl ketone, neutralizing the aqueous phase with a mineral or organic acid or by passing it through an acidic resin, preferably through an acidic resin, concentrating and then co-evaporating with an organic solvent chosen from ethanol, methanol, toluene and/or isopropanol, drying the product obtained under vacuum, and then optionally purifying it by chromatography and/or crystallization.

Detailed examples for the preparation of the C-glycoside derivatives corresponding to formula (II) as defined above and for which X corresponds to —CO— are given in the examples which follow, without, however, limiting the invention.

The synthetic process according to the invention has the advantage of allowing quick and easy access to the novel C-glycoside derivatives corresponding to formula (II) as defined above and for which X corresponds to —CO—, due to the fact that they are obtained in a single step using water as solvent or in a mixture consisting of water and a water-miscible solvent, the water or the said mixture being compatible with the chemistry of sugars containing hydroxyl functions in free form.

In addition, the yields are excellent and virtually quantitative.

The C-glycoside derivatives of formula (II) for which X corresponds to —CH(OH)—, —CH(NR$_1$R$_2$)—, —CHR'— or —C(=CHR')—, are obtained from the C-glycoside derivatives of formula (II) for which X corresponds to —CO— via processes that are well known to those skilled in the art, for instance those described in Advanced Organic Chemistry, Reactions, Mechanisms and Structure, Jerry March (IV Edition) 1992. These processes may optionally require the protection and deprotection of the hydroxyl functions, these protection and deprotection methods also being well known to those skilled in the art, for instance those described in the document *Protective Groups in Organic Synthesis*, T. W. Greene, P. G. M. Wuts (Wiley Interscience).

In addition, some of the hydroxyl functions of the C-glycoside derivatives of formula (II) may be sulfated after selective protection of the other hydroxyl functions. This sulfatation reaction after protection is described especially by A. Lubineau in the reference J. Chem. Soc. Chem. Commun., 1993, page 1419.

Detailed examples for the preparation of the compounds according to the invention are moreover given in the examples to follow.

This invention also features compositions which comprises at least one C-glycoside derivative corresponding to formula (II) as defined above.

The compositions according to the invention may comprise the C-glycoside derivatives corresponding to formula (II) alone or as mixtures in all proportions.

The amount of C-glycoside derivatives corresponding to formula (II) that may be formulated into the compositions according to the invention obviously depends on the desired effect and should be in an amount that is sufficient to stimulate the synthesis of hyaluronic acid and proteoglycans by fibroblasts and keratinocytes.

To provide an order of magnitude, the compositions of the invention may contain at least one C-glycoside derivative corresponding to formula (II) in an amount representing from 0.00001% to 25% relative to the total weight of the composition, and preferably in an amount representing from 0.0001% to 10% relative to the total weight of the composition.

The compositions according to the invention are suited for cosmetic or pharmaceutical application, particularly dermatological application. Preferably, the compositions according to the invention are suited for cosmetic application.

Advantageously, the compositions according to the invention are compositions for washing and/or making up and/or removing makeup from the skin of the body and/or the face and/or mucous. membranes (for example the lips) and/or the scalp and/or the hair and/or the nails and/or the eyelashes and/or the eyebrows.

This invention also features the administration of the compositions as defined above for the cosmetic treatment of keratin materials, such as the hair, facial and/or body skin, the eyelashes, the eyebrows, the nails and mucous membranes.

This invention also features the administration of the compositions as defined above for improving the appearance of keratin materials.

The composition according to the invention may be ingested, injected or applied to the skin (to any area of body skin), the hair, the nails or mucous membranes (buccal, jugal, gingival, genital or conjunctival mucous membranes).

Depending on the mode of administration, the composition of the invention may be in any presentation form normally used, particularly in cosmetology.

A preferred composition of the invention is a cosmetic composition for topical application.

For topical application to the skin, the composition that may be administered according to the invention may be especially in the form of an aqueous or oily solution or of a dispersion of the lotion or serum type, of emulsions of liquid or semi-liquid consistency of the milk type, obtained by dispersing a fatty phase in an aqueous phase (O/W) or conversely (W/O), or of suspensions or emulsions of soft consistency of the aqueous or anhydrous gel or cream type, or alternatively of microcapsules or microparticles, or of vesicular dispersions of ionic and/or nonionic type. These compositions are prepared according to the usual methods.

The compositions according to the invention obviously comprise a cosmetically acceptable support and may be in any presentation form normally used for topical application, especially in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, these spherules possibly being polymer nanoparticles such as nanospheres and nanocapsules or better still lipid vesicles of ionic and/or nonionic type.

These compositions may be more or less fluid and may have the appearance of a white or colored cream, an ointment, a milk, a lotion, a serum, a paste or a mousse. It may optionally be applied to the skin in the form of an aerosol. It may also be in solid form, for example in the form of a stick. It may be used as a care product, as a cleansing product, as a makeup product or as a simple deodorant product.

The compositions that may be administered according to the invention may also be a hair care composition, and especially a shampoo, a hair setting lotion, a treating lotion, a styling cream or gel, a dye composition (especially oxidation dyes) optionally in the form of coloring shampoos, restructuring lotions for the hair, a permanent-waving composition (especially a composition for the first stage of a permanent-waving operation), a lotion or gel for preventing hair loss, an antiparasitic shampoo, etc.

The amounts of the various constituents of the compositions that may be used according to the invention are those that are conventionally used in the fields under consideration.

These compositions especially constitute cleansing, protecting, treating or care creams for the face, for the hands, for the feet, for the major anatomical folds or for the body (for example day creams, night creams, makeup-removing creams, foundation creams or antisun creams), fluid foundations, makeup-removing milks, protective or care body milks, after-sun milks, skincare lotions, gels or mousses, for instance cleansing lotions, antisun lotions or artificial tanning lotions, bath compositions, deodorizing compositions comprising a bactericidal agent, aftershave gels or lotions, hair-removing creams, compositions for treating insect bites, pain-relief compositions and compositions for treating certain skin diseases, for instance eczema, rosacea, psoriasis, lichens and severe pruritus.

The compositions according to the invention may also be solid preparations constituting cleansing bars or soaps.

The compositions according to the invention may also be packaged in the form of an aerosol composition also comprising a propellant under pressure.

When the composition according to the invention is an emulsion, the proportion of the fatty phase may range from 5% to 80% by weight and preferably from 5% to 50% by weight relative to the total weight of the composition. The oils, waxes, emulsifiers and co-emulsifiers used in the composition in emulsion form are chosen from those conventionally used in cosmetics. The emulsifier and co-emulsifier are present in the composition in a proportion ranging from 0.3% to 30% by weight and preferably from 0.5% to 20% by weight relative to the total weight of the composition. The emulsion may also contain lipid vesicles.

When the composition according to the invention is an oily solution or gel, the fatty phase may represent more than 90% of the total weight of the composition.

In a known manner, the compositions of the invention may also contain adjuvants or additives that are common in cosmetics or dermatology, such as hydrophilic or lipophilic gelling agents, hydrophilic or lipophilic active agents, preservatives, antioxidants, solvents, fragrances, fillers, screening agents, pigments, chelating agents, odor absorbers and dyestuffs and colorants. The amounts of these various adjuvants are those conventionally used in the fields under consideration, for example from 0.01% to 20% of the total weight of the composition. Depending on their nature, these adjuvants may be introduced into the fatty phase, into the aqueous phase, into lipid vesicles and/or into nanoparticles.

When the composition of the invention is an emulsion, the proportion of the fatty phase may range from 5% to 80% by weight and preferably from 5% to 50% by weight relative to the total weight of the composition. The oils, emulsifiers and co-emulsifiers used in the composition in emulsion form are chosen from those conventionally used in the field under consideration. The emulsifier and co-emulsifier are present in the composition in a proportion ranging from 0.3% to 30% by weight and preferably from 0.5% to 20% by weight relative to the total weight of the composition.

As oils or waxes that may be used in the invention, mention may be made of mineral oils (liquid petroleum jelly), plant oils (liquid fraction of karite butter or sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) may be added to these oils. As emulsifiers that may be used in the invention, examples that may be mentioned include glyceryl stearate, polysorbate 60 and the mixture of PEG-6/PEG-32/glycol stearate sold under the name Tefose® 63 by Gattefosse.

As solvents that may be used in the invention, mention may be made of lower alcohols, especially ethanol and isopropanol, and propylene glycol.

As emulsifiers and co-emulsifiers that may be used in the invention, examples that may be mentioned include fatty acid esters of polyethylene glycol, such as PEG-40 stearate and PEG-100 stearate, and fatty acid esters of polyols, such as glyceryl stearate and sorbital tristearate.

As hydrophilic gelling agents that may be used in the invention, mention may be made of carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, mention may be made of modified clays, for instance bentones, metal salts of fatty acids, for instance aluminum stearates and hydrophobic silica, ethylcellulose and polyethylene.

At least one C-glycoside derivative of formula (II) may be used in the preparation of cosmetic and/or pharmaceutical compositions, particularly dermatological compositions, suited to stimulate or to treat the synthesis or secretion of GAGs and/or PGs, with a view to correcting the negative effects of the said insufficiencies, in particular to improve the functional state of the cells of the skin, especially of the dermis.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Example of a C-Glycoside Derivative of Xylose

Synthesis of C-β-D-xylopyranoside-n-propan-2-one of formula (i):

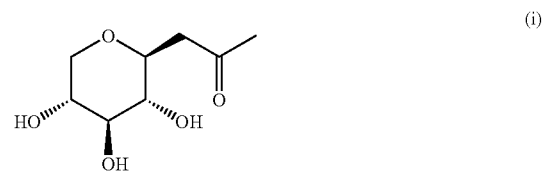

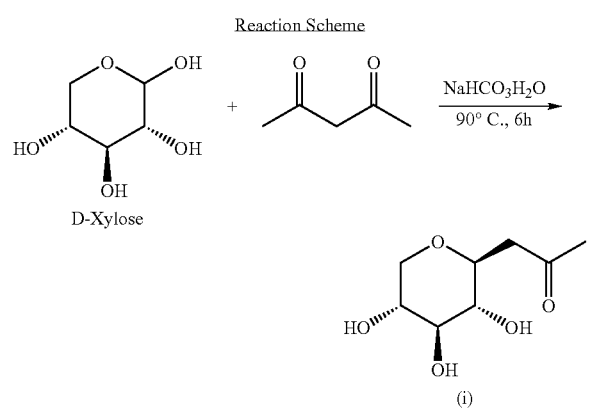

Procedure:

D-Xylose (1 g, 6.66 mmol) was dissolved in 10 ml of water in a 25 ml three-necked flask equipped with a condenser, a thermometer and a magnetic stirrer, followed by addition of 2,4-pentanedione (0.82 ml, 8 mmol) and sodium bicarbonate (839 mg, 10 mmol). The mixture was stirred for 6 hours at 90° C. The reaction medium was then washed with dichloromethane (twice 5 ml). The aqueous phase was passed through a Dowex 50X-200 resin which had been preconditioned with aqueous washes (the final solution was at pH 3-4). The eluate was concentrated and then co-evaporated with ethanol.

The light brown oil obtained was dried under vacuum (600 mg, i.e., a yield of 76%).

$^1$H NMR: in accordance with the expected structure.

EXAMPLE 2

Example of C-Glycoside Derivatives of Fucose

With L-fucose as the starting material, this method provided a mixture of 2 isomers:
1-(C-β-L-fucopyranoside)propan-2-one, of formula (ii), and
1-(C-β-L-fucofuranosyl)propan-2-one, of formula (iii).

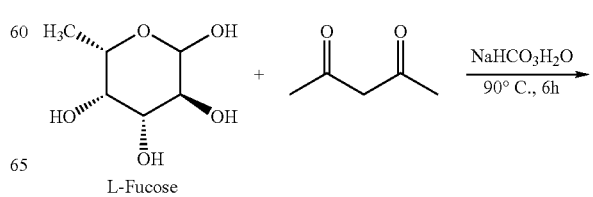

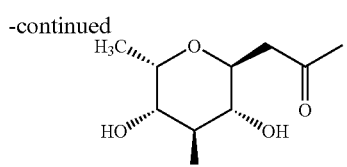

(ii) 57%

+

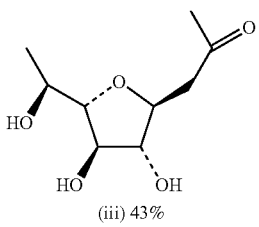

(iii) 43%

Procedure:

L-Fucose (0.913 g, 5.56 mmol) was dissolved in 10 ml of water in a 25 ml three-necked flask equipped with a condenser, a thermometer and a magnetic stirrer, followed by addition of 2,4-pentanedione (0.685 ml, 6.67 mmol) and sodium bicarbonate (0.70 g, 8.34 mmol). The mixture was stirred for 6 hours at 90° C. The reaction medium was then washed with dichloromethane (twice 15 ml). The aqueous phase was passed through a Dowex 50X-200 resin which had been preconditioned with aqueous washes (the final solution was at pH 3-4). The eluate was concentrated and then co-evaporated with ethanol.

The yellow oil obtained was dried under vacuum (674 mg, i.e. a yield of 59%). The oil was chromatographed on silica gel (eluent: MeOH/CH$_2$Cl$_2$ (1/9))

EXAMPLE 3

Example of Protection of a C-Glycoside Derivative of Xylose

Synthesis of C-β-D-(3,4,5-triacetoxy)xylopyranoside-n-propan-2-one of formula (iv)

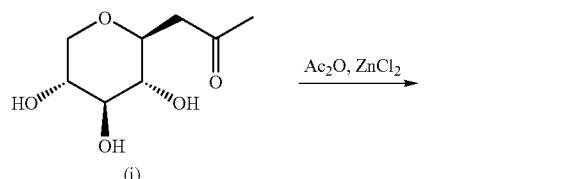

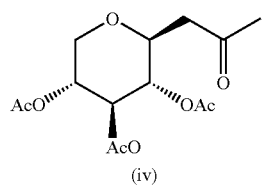

1-(3,4,5-Trihydroxytetrahydropyran-2-yl)propan-2-one (5.56 mmol) was dissolved in 10 ml of acetic anhydride in a three-necked flask, and a catalytic amount of ZnCl$_2$ was added. The mixture was stirred overnight at room temperature. After stirring overnight, the mixture was diluted with ethyl acetate and the organic phase was washed with saturated NaHCO$_3$ solution and then washed three times with water, dried over MgSO$_4$, filtered and evaporated. The peracetylated sugar was obtained in quantitative yield.

EXAMPLE 4

Example of Reduction of Ketone to Hydroxyl in a C-Glycoside Derivative of Xylose (C-Glycoside Derivative of Formula (I) for which X Corresponds to —CH(OH)—)

Synthesis of C-β-D-xylopyranoside-2-hydroxypropane of formula (vi):

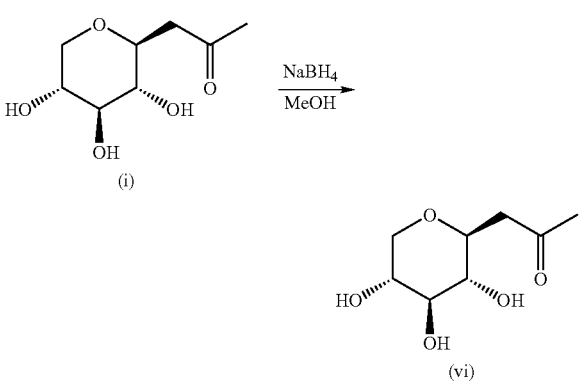

The xylose derivative (5.56 mmol) was dissolved in 10 ml of methanol in a 25 ml round-bottomed flask and cooled to 0° C. Sodium borohydride (7 mmol) was added portionwise and the reaction medium was then left to cool to room temperature and stirred for 15 hours. The mixture was cooled to 0° C., 5 ml of water and hydrochloric acid solution (1N) were added until a reaction medium of pH 1 was obtained, and the resulting mixture was then extracted three times with butanol. The organic phase was washed twice with saturated sodium chloride solution and then dried over sodium sulfate, filtered and concentrated to the maximum. A yellow oil was obtained.

EXAMPLE 5

Example of Reductive Alkylation of Ketone to Amine in a C-Glycoside Derivative of Xylose (C-Glycoside Derivative of Formula (I) for which X Corresponds to —CH(NR$_1$R$_2$)—)

Synthesis of C-β-D-xylopyranoside-2-phenylaminopropane of formula (vii)

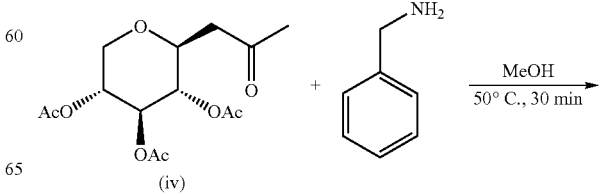

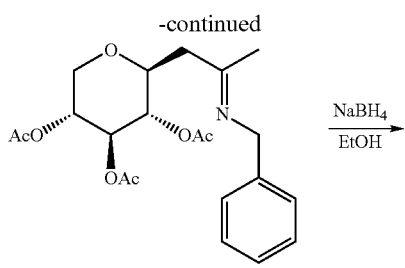

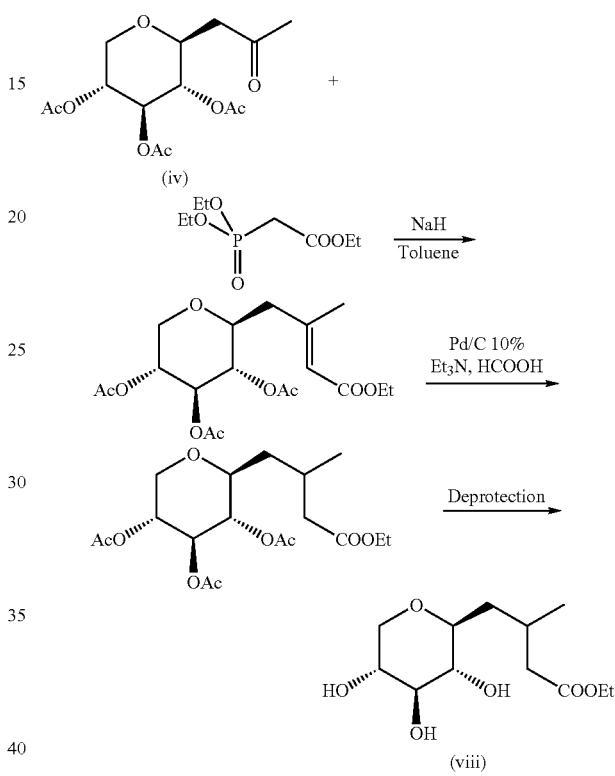

EXAMPLE 6

Example of Conversion of Ketone to an Alkyl Chain via a Wittig Reaction on a C-Glycoside Derivative of Xylose (C-Glycoside Derivative of Formula (I) for which X Corresponds to —CHR'—)

Synthesis of ethyl 3-methyl4-(C-β-D-xylopyranoside)-butyrate of formula (viii):

C-β-D-(3,4,5-Triacetoxy)xylopyranoside-n-propan-2-one (1 g, 3.20 mmol) was dissolved in 15 ml of methanol in a 25 ml three-necked flask equipped with a condenser, a thermometer and a magnetic stirrer, followed by addition of benzylamine (0.34 g, 50° C., 30 min Deprotection 3.20 mmol). The mixture was stirred for 30 minutes at 50° C. The reaction medium was concentrated to the maximum. An oil was obtained, which was dried under vacuum. This oil was diluted in 15 ml of ethanol and sodium borohydride (0.12 g, 3.20 mmol) was then added portionwise. The reaction medium was then stirred for 2 hours. The mixture was cooled to 0° C., 5 ml of water and hydrochloric acid solution (1N) were added until a reaction medium of pH 1 was obtained, and the mixture was then extracted. The organic phase was washed twice with saturated sodium chloride solution and then dried over sodium sulfate, filtered and concentrated to the maximum. An oil was obtained.

The deprotection step was performed according to the general procedure described below in Example 8.

Wittig reaction:

0.03 mmol of NaH (dispersion in oil) was dissolved in 50 ml of anhydrous toluene, under nitrogen, in a 50 ml three-necked flask equipped with a condenser, a thermometer and a magnetic stirrer. 0.03 mmol of triethyl phosphonoacetate was added dropwise to this solution while maintaining the temperature between 30°-35° C. After addition, the mixture was stirred for 1 hour at room temperature. 0.03 mmol of 1-(3,4,5-triacetoxytetrahydropyran-2-yl)propan-2-one in 5 ml of anhydrous toluene was added dropwise to this clear solution, while maintaining the temperature at 20°-25° C. After addition, the mixture was heated at 60°-65° C. for 15 minutes and then cooled to 15°-20° C. The precipitate formed was decanted off and the pasty product was washed three times with toluene at 60° C. (note: the decantation was performed each time at room temperature). The toluene phases were combined and evaporated to dryness, and the product obtained was Deprotection Toluene separated out on a column of silica gel. A solid was obtained.

Reduction of the double bond:

0.1 mmol of starting material was dissolved in 10 ml of ethanol and hydrogenated at 8 bar in the presence of Pd/C (10%). After 3 hours, the reaction was filtered through Celite and the filtrate was then evaporated.

The deprotection step was performed according to the general procedure described below in Example 8.

EXAMPLE 7

Step of Deprotection of the O-Acetyl Functions

A solution of acetylated derivative of xylose (5 mmol) in 10 ml of methanol was prepared. 3 molar equivalents of sodium methoxide (NaOMe) were added and the mixture was stirred for 3 to 12 hours. The methanol was evaporated off and the residue was diluted with water. The aqueous phase was passed through a Dowex 50X-200 resin which had been preconditioned with aqueous washes (the final solution was at pH 3-4). The eluate was concentrated and then co-evaporated with ethanol.

The oil obtained was dried under vacuum.

EXAMPLE 8

1-Phenyl-2-(C-β-D-Xylopyranoside)Ethan-1-One

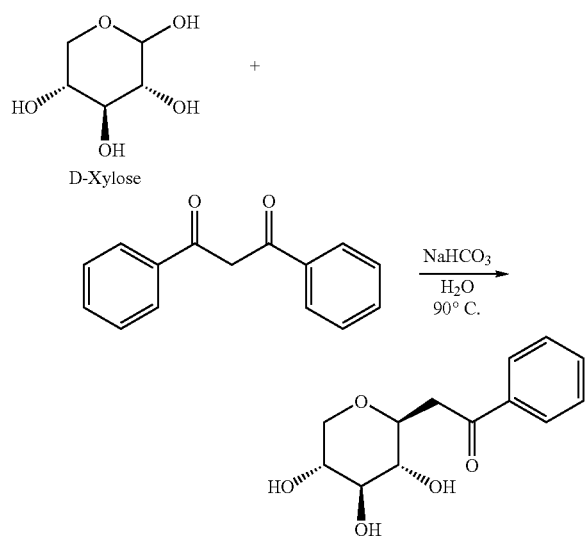

1 equivalent of D-xylose (0.0333 mol; 5 g) was dissolved in about 50 ml of water in a 250 ml three-necked flask; 1.5 equivalents of sodium hydrogen carbonate (0.4995 mol; 4.2 g), 50 ml of water and 1.2 equivalents of dibenzoylmethane (0.0399 mol; 9 g) were added portionwise by spatula (exothermic reaction).

The mixture was heated at 90° C. for 6 hours.

The reaction medium was allowed to return to room temperature and the precipitate formed was filtered off (this precipitate corresponds to the excess dibenzoyhnethane); 2 successive extractions with dichloromethane were performed and the aqueous phase was extracted with 2 fractions of 50 ml of butanol; the butanol phase was then washed with 2 fractions of 50 ml1 of saturated aqueous NaCl. The organic butanol phase recovered was concentrated to dryness and the precipitate formed was dissolved in water and passed through a Dowex 50 W 2.200 ion exchange resin; the recovered fractions were concentrated to dryness.

The precipitate obtained was purified on a column of silica using a mixture of 3% methanol/97% dichloromethane as eluent.

480 mg of a beige-colored precipitate were obtained.

EXAMPLE 9

1-[2-(3-Hydroxypropylamio)Propyl]-C-β-D-Xylopyranose

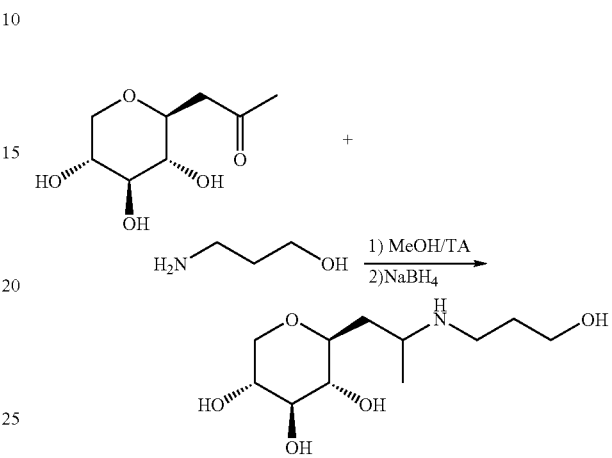

1 equivalent of 1-(3,4,5-trihydroxytetrahydropyran-2-yl)propan-2-one (2.6316 mmol; 500 mg) was dissolved in about 20 ml of methanol in a 50 ml three-necked flask; 1 equivalent of 3-amino-1-propanol (2.6316 mmol; 0.2 ml) was added and the mixture was stirred at room temperature for 6 hours. 1.4 equivalents of sodium borohydride (3.684 mmol; 140 mg) were added portionwise by spatula (exothermic reaction) and the mixture was stirred at room temperature for 12 hours.

The reaction medium was concentrated to dryness and the oil obtained was diluted in the minimum amount of ethanol; this mixture was passed through a silica sinter so as to remove the boron salts; the filtrate was concentrated to dryness.

100 mg of a beige-colored oil were obtained (yield=15%).

EXAMPLE 10

Studies of the Effect of C-Glycoside Derivatives on Synthesis of Hyaluronic Acid The study was performed by measuring the incorporation of radioactive glucosamine into the matrix neosynthesized by normal human dermal fibroblast cultures. The incorporation of radioactive glucosamine indicated a specific neosynthesis of glycosaminoglycans via incorporation of the acetylated form of this glucosamine.

The fibroblast cultures were prepared according to the standard methods of cell culturing, i.e., in MEM/M199 medium sold by Gibco, in the presence of sodium bicarbonate (1.87 mg/ml), L-glutamine (2 mM), penicillin (50 IU/ml) and 10% foetal calf serum (Gibco).

The test was performed on a cell culture at 80% confluence, on 96-well plates. The C-glycoside derivative at concentrations of 0.1 to 30 mM was placed in contact with the cells for 48 hours. Labeling with radioactive glucosamine (D-[6-H$^3$]-glucosamine, Amersham TRK398 (814 Gbq/mmol, 22 Ci/mmol)) was performed for 24 hours.

The level of radioactive glucosamine incorporated was measured at the end of the test by adsorption of the anionic molecules onto Q-sepharose beads followed by desorption of the sparingly and moderately anionic molecules with 6M urea plus 0.2M NaCl. Once washed, the radioactivity incorporated into the highly cationic molecules remaining on the support was counted.

The results were evaluated relative to a control consisting of cells that have not been treated with the C-glycoside derivative of formula (I).

A positive control (TGFβ at 10 ng/ml) known to stimulate GAG synthesis was introduced into the test as positive reference.

The results are reported in the following Table:

TABLE

| TREATMENT | | | VALUE | sd | n | % | p |
|---|---|---|---|---|---|---|---|
| Control (culture medium) | | | 7793-7681 | 274-176 | 3—3 | 100—100 | — |
| Positive control (TGFβ) | | | 27124-34865 | 947-2849 | 3—3 | 348-454 | <0.01 |
| | | | | | | | <0.01 |
| D-Xylose | 0.5 | mM | 4063 | 347 | 3 | 86 | >0.05 |
| | 0.1 | mM | 6586 | 489 | 3 | 102 | >0.05 |
| C-β-D-Xylo- | 3 | mM | 18271 | 1373 | 3 | 218 | p < 0.01 |
| pyranoside-2- | 1 | mM | 14209 | 1799 | 3 | 169 | p < 0.01 |
| hydroxypropane | 0.3 | mM | 11634 | 626 | 3 | 139 | p < 0.05 |
| 1-Phenyl-2-(C- | 1 | mM | 7941 | 172 | 3 | 95 | p > 0.05 |
| β-D-xylopyrano- | 0.3 | mm | 8545 | 653 | 3 | 102 | p > 0.05 |
| side)ethan-1-one | 0.1 | mM | 10113 | 890 | 3 | 120 | p > 0.05 |
| 1-[2-(3- | 1 | mM | 14832 | 343 | 3 | 140 | p < 0.01 |
| Hydroxypropyl- | 0.3 | mM | 11585 | 804 | 3 | 109 | p > 0.05 |
| amino)proprl])- | 0.1 | mM | 11656 | 1084 | 3 | 110 | p > 0.05 |
| C-β-D-xylo- | | | | | | | |
| pyranose | | | | | | | |
| C-β-D-Xylo- | 10 | mM | 12507-9811 | 1201 | 3 3 | 161 | <0.01 |
| pyranoside-n- | 2 | mM | 11014 | 639 | 3 | 131 | >0.05 |
| propan-2-one | 0.4 | mM | 8564 | 625 | 3 | 141 | <0.01 |
| | | | | | | | >0.05 |

The measured values are given in counts per minute (cpm)
sd: standard deviation
p: confidence interval
n: replicates These results evidence that:
C-β-D-xylopyranoside-n-propan-2-one stimulates the incorporation of radioactive glucosamine between concentrations of 0.4, 2 and 10 mM;
C-β-D-xylopyranoside-2-hydroxypropane stimulates the incorporation of radioactive glucosamine at concentrations of 0.1, 0.3 and 1 mM;
1-phenyl-2-(C-β-D-xylopyranoside)ethan-1-one and 1-[2-(3-hydroxypropylamino)propyl]-C-β-D-xylopyranose stimulate the incorporation of radioactive glucosamine at concentrations of 0.3, 1 and 3 mM.

Thus, the C-glycoside derivatives according to the invention stimulate the incorporation of radioactive glucosamine, which indicates a neosynthesis of glycosaminoglycans via incorporation of the acetylated form of this glucosamine.

EXAMPLE 11

Compositions According to the Invention

Composition 1: Oil-in-Water (O/W) Cream

| | |
|---|---|
| Glyceryl monostearate | 6.0% |
| Stearyl alcohol | 4.0% |
| Liquid petroleum jelly | 10.0% |
| Silicone oil | 5.0% |

-continued

| | |
|---|---|
| C-β-D-Xylopyranoside-n-propan-2-one | 10.0% |
| Glycerol | 8.0% |
| Carboxyvinyl polymer of Carbopol type | 0.3% |
| Preservatives | 0.4% |
| Fragrance | 0.5% |
| Triethanolamine | 0.3% |
| Water qs | 100% |

Composition 2: Water-in-Oil (W/O) Cream

| | |
|---|---|
| Octyldodecanol | 10.0% |
| Magnesium stearate | 4.0% |
| Natural beeswax | 5.0% |
| Sorbitan sesquioleate | 4.5% |
| Glyceryl monostearate and | 1.0% |
| distearate and potassium stearate | |
| Liquid petroleum jelly | 22.0% |
| Jojoba oil | 4.0% |
| C-β-D-Xylopyranoside-n-propan-2-one | 2.5% |
| Preservatives | 0.4% |
| Fragrance | 0.6% |
| Water qs | 100% |

Composition 3: Moisturizing Gel

| | |
|---|---|
| C-β-D-Xylopyranoside-n-propan-2-one | 5.0% |
| Glycerol | 12.0% |
| Acrylamide/sodium | 5.0% |
| 2-acrylamidomethyl-propanesulfonate | |
| copolymer at 40% in isoparaffin/water (Sepigel 305) | |
| Mixture of polydimethylsiloxane | 2.0% |
| containing α-hydroxylated groups and | |
| of cyclopentadimethylsiloxane (15/85) | |

-continued

| Preservatives | 0.4% |
| --- | --- |
| Fragrance | 0.6% |
| Water qs | 100% |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition comprising:
   a cosmetically and/or physiologically acceptable medium,
   at least one cosmetically acceptable additive chosen from moisturizing agents, sunscreen agents, and emulsifiers, and
   at least one C-glycoside of formula (I):

$$S—CH_2—X—R \qquad (I)$$

and cosmetically and/or physiologically acceptable salts thereof,
   in which
   S is a xylose sugar moiety in pyranose or furanose form, and of L or D configuration;
   the bond S—CH$_2$X is an anomeric-C bond;
   X is chosen from —CO—, —CH(OH)—, and —CH(NHR$_1$)—; and
   R is chosen from linear or branched, saturated or unsaturated alkyl, perfluoroalkyl, and hydrofluoroalkyl radicals; from cycloalkyl, cycloperfluoroalkyl and cyclohydrofluoroalkyl radicals comprising from 1 to 18 carbon atoms; and from phenyl and benzyl radicals;
   wherein said radicals are optionally interrupted with at least one hetero atom chosen from oxygen, sulfur, nitrogen and silicon, and
   wherein said radicals are optionally substituted with:
   at least one radical chosen from —OR'$_1$, —SR"$_1$, —NR'"$_1$R'$_2$, COOR"$_2$, —CONHR'"$_2$, —CN, halogen, perfluoroalkyl, and hydrofluoroalkyl radicals; and/or
   at least one radical chosen from cycloalkyl radicals, heterocyclic radicals, and unsubstituted aryl radicals,
   the radical R$_1$ is chosen from radicals R, hydrogen, and hydroxyl; and
   the radicals R'$_1$, R'$_2$, R"$_1$, R"$_2$, R'"$_1$ and R'"$_2$, which may be identical or different, are each chosen from hydrogen, from linear or branched, saturated or unsaturated alkyl radicals, and from radicals chosen from hydroxyl, perfluoroalkyl and/or hydrofluoroalkyl radicals having from 1 to 30 carbon atoms, and
   wherein said at least one C-glycoside of formula (I) is present in an amount ranging from 0.00001% to 25% by weight, relative to the total weight of the composition.

2. The composition of claim 1, wherein S is a xylopyranoside of D and/or L configuration, X is a —CO— radical, and R is chosen from unsubstituted alkyl radicals comprising from 1 to 18 carbon atoms, and from unsubstituted phenyl radicals.

3. The composition of claim 2, wherein R is a methyl radical or a unsubstituted phenyl radical.

4. The composition of claim 1, wherein S is a xylopyranoside of D and/or L configuration, X is a —CH(OH)— radical, and R is chosen from unsubstituted alkyl radicals comprising from 1 to 18 carbon atoms.

5. the composition of claim 4, wherein R is a methyl radical.

6. The composition of claim 1, wherein S is a xylopyranoside of D and/or L configuration, X is —CH(NHR$_1$)—, R is chosen from linear or branched, saturated or unsaturated alkyl, perfluoroalkyl, and hydrofluoroalkyl radicals; from cycloalkyl, cycloperfluoroalkyl, and cyclohydrofluoroalkyl radicals comprising from 1 to 18 carbon atoms, and R$_1$ is chosen from benzyl radicals and alkyl radicals substituted with at least one hydroxyl radical.

7. the composition of claim 6, wherein R is a linear or branched saturated alkyl radical comprising from 1 to 18 carbon atoms, and R$_1$ is chosen from benzyl radicals and alkyl radicals substituted with at least one hydroxyl radical.

8. The composition of claim 6, wherein R is a methyl radical and R$_1$ is chosen from an ethyl radical substituted with at least one hydroxyl radical and a benzyl radical.

9. The composition of claim 1, wherein said at least one C-glycoside of formula (I) is chosen from:
   —C-β-D-xylopyranoside-n-propan-2-one;
   —C-α-D-xylopyranoside-n-propan-2-one;
   -1-phenyl-2-(C-β-D-xylopyranoside)ethan-1-one;
   -1-phenyl-2-(C-α-D-xylopyranoside)ethan-1-one;
   -1-[2-(3-hydroxypropylamino)propyl]-Cβ-D-xylopyranose
   -1-[2-(3-hydroxypropylamino)propyl]-C-α-D-xylopyranose
   —C-β-D-xylopyranoside-2-hydroxypropane;
   —C-α-D-xylopyranoside-2-hydroxypropane;
   optical isomers thereof, and cosmetically and/or physiologically acceptable salts thereof.

10. The composition of claim 9, wherein said at least one C-glycoside of formula (I) is chosen from C-β-D-xylopyranoside-2-hydroxypropane and C-α-D-xylopyranoside-2-hydroxypropane.

11. The composition of claim 1, wherein said moisturizing agents are chosen from polyols.

12. The composition of claim 1, wherein said moisturizing agents are chosen from propylene glycol and glycerine.

13. The composition of claim 1, wherein said emulsifiers are present in an amount ranging from 0.3% to 30% by weight, relative to the total weight of the composition.

14. The composition of claim 13, wherein said emulsifiers are present in an amount ranging from 0.5% to 20% by weight, relative to the total weight of the composition.

15. The composition of claim 1, wherein said emulsifiers are chosen from fatty acid esters of polyethylene glycol and fatty acid esters of polyols.

16. The composition of claim 15, wherein said fatty acid esters of polyethylene glycol are chosen from PEG-40 stearate and PEG-100 stearate.

17. The composition of claim 15, wherein said fatty acid esters of polyols are chosen from glyceryl stearate and sorbitan tristearate.

18. The composition of claim 1, wherein said emulsifiers are chosen from glyceryl stearate, polysorbate 60, and a mixture of PEG-6/PEG-32/glycol stearate.

19. The composition of claim 1, wherein said at least one C-glycoside of formula (I) is present in an amount ranging from 0.0001 to 10% by weight, relative to the total weight of the composition.

20. A make-up removing composition comprising:
a cosmetically and/or physiologically acceptable medium, and
at least one C-glycoside derivative of formula (I):

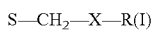

and cosmetically and/or physiologically acceptable salts thereof,
in which
S is a xylose sugar moiety in pyranose or furanose form, and of L or D configuration;
the bond S—CH$_2$X is an anomeric-C bond;
X is a group chosen from —CO—, —CH(OH)—, and —CH(NHR$_1$)—;
wherein
R is chosen from linear or branched, saturated or unsaturated alkyl, perfluoroalkyl, and hydrofluoroalkyl radicals; from cycloalkyl, cycloperfluoroalkyl and cyclohydrofluoroalkyl radicals comprising from 1 to 18 carbon atoms; and from phenyl and benzyl radicals;
wherein said radicals are optionally interrupted with at least one hetero atom chosen from oxygen, sulfur, nitrogen and silicon, and
wherein said radicals are optionally substituted with:
at least one radical chosen from —OR'$_1$, —SR"$_1$, —NR'''$_1$R'$_2$, —COOR"$_2$, —CONHR'''$_2$, —CN, halogen, perfluoroalkyl, and hydrofluoroalkyl radicals; and/or
at least one optionally substituted radical chosen from cycloalkyl, and heterocyclic radicals, and/or at least one unsubstituted aryl radical,
the radical R$_1$ is chosen from radicals R, hydrogen, and hydroxyl; and
the radicals R'$_1$, R'$_2$, R"$_1$, R"$_2$, R'''$_1$ and R'''$_2$, which may be identical or different, are each chosen from hydrogen, from linear or branched, saturated or unsaturated alkyl radicals, and from radicals chosen from hydroxyl, perfluoroalkyl and/or hydrofluoroalkyl radicals having from 1 to 30 carbon atoms, and
wherein said at least one C-glycoside of formula (I) is present in an amount ranging from 0.00001% to 25% by weight, relative to the total weight of the composition.

* * * * *

UNITED STATES PATENT AND TRADEMARK OFFICE
CERTIFICATE OF CORRECTION

PATENT NO. : 7,732,414 B2
APPLICATION NO. : 11/373485
DATED : June 8, 2010
INVENTOR(S) : Maria Dalko et al.

It is certified that error appears in the above-identified patent and that said Letters Patent is hereby corrected as shown below:

Claim 3, col. 34, line 2, "a unsubstituted" should read -- an unsubstituted --.

Claim 5, col. 34, line 7, "the" should read -- The --.

Claim 7, col. 34, line 17, "the" should read -- The --.

Signed and Sealed this

Seventeenth Day of August, 2010

David J. Kappos
*Director of the United States Patent and Trademark Office*